United States Patent
Nakano et al.

(10) Patent No.: US 10,046,276 B2
(45) Date of Patent: Aug. 14, 2018

(54) SENSOR CONTROL METHOD AND SENSOR CONTROL APPARATUS

(71) Applicant: NGK SPARK PLUG CO., LTD., Nagoya-shi, Aichi (JP)

(72) Inventors: Yoshihiro Nakano, Komaki (JP); Shiro Kakimoto, Kasugai (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 371 days.

(21) Appl. No.: 14/857,037

(22) Filed: Sep. 17, 2015

(65) Prior Publication Data
US 2016/0082390 A1 Mar. 24, 2016

(30) Foreign Application Priority Data

Sep. 24, 2014 (JP) .................. 2014-193809
Aug. 5, 2015 (JP) .................. 2015-155267

(51) Int. Cl.
| | |
|---|---|
| B01D 53/94 | (2006.01) |
| F01N 3/20 | (2006.01) |
| F01N 13/00 | (2010.01) |
| G05B 15/02 | (2006.01) |
| G05D 7/06 | (2006.01) |
| G01N 27/407 | (2006.01) |
| G01N 27/417 | (2006.01) |

(52) U.S. Cl.
CPC ......... *B01D 53/9431* (2013.01); *F01N 3/206* (2013.01); *F01N 3/208* (2013.01); *F01N 13/008* (2013.01); *G01N 27/4074* (2013.01); *G05B 15/02* (2013.01); *G05D 7/0629* (2013.01); *B01D 53/9418* (2013.01); *B01D 53/9495* (2013.01); *B01D 2258/012* (2013.01); *F01N 2560/021* (2013.01); *F01N 2560/026* (2013.01); *F01N 2900/0414* (2013.01); *F01N 2900/0422* (2013.01); *F01N 2900/1402* (2013.01); *G01N 27/417* (2013.01)

(58) Field of Classification Search
None
See application file for complete search history.

(56) References Cited

U.S. PATENT DOCUMENTS

| | | | |
|---|---|---|---|
| 2011/0048970 A1 | 3/2011 | Sugaya et al. | |
| 2012/0145543 A1* | 6/2012 | Sugaya | G01N 27/4074 204/424 |

FOREIGN PATENT DOCUMENTS

JP 2011-075546 A 4/2011

* cited by examiner

*Primary Examiner* — Jill A Warden
*Assistant Examiner* — Matthew D Krcha
(74) *Attorney, Agent, or Firm* — Stites & Harbison, PLLC; Jeffrey A. Haeberlin; James R. Hayne

(57) ABSTRACT

In a multi-gas sensor control apparatus 1, the concentrations of ammonia, $NO_2$, and NO contained in a gas under measurement are computed as a result of execution of gas concentration computation processing by a CPU 61 of a microcomputer 60. In the gas concentration computation processing, depending on whether or not a correction permission condition is satisfied (S200), the CPU 61 switches its operation between an operation of storing the latest corrected ammonia concentration as a value of "$NH_3$ concentration (this time)" (S170) and an operation of storing a value of "$NH_3$ concentration (reference)" as a value of "$NH_3$ concentration (this time)" (S210). The multi-gas sensor control apparatus 1 can suppress a decrease in the accuracy of detection of the ammonia concentration performed through use of a multi-gas sensor 2.

16 Claims, 12 Drawing Sheets

63a — FIRST PUMPING CURRENT – OXYGEN CONCENTRATION RELATIONAL EXPRESSION

63b — AMMONIA CONCENTRATION OUTPUT – AMMONIA CONCENTRATION RELATIONAL EXPRESSIONS FOR DIFFERENT OXYGEN CONCENTRATIONS

63c — SECOND PUMPING CURRENT – NO CONCENTRATION RELATIONAL EXPRESSIONS FOR DIFFERENT AMMONIA CONCENTRATIONS

63d — NEGATIVE AMMONIA CONCENTRATION OUTPUT – $NO_2$ CONCENTRATION RELATIONAL EXPRESSION

63e — CONTRIBUTIVE SECOND PUMPING CURRENT – NO CONCENTRATION, $NO_2$ CONCENTRATION RELATIONAL EXPRESSION

63f — AMMONIA CONCENTRATION OUTPUT – AMMONIA CONCENTRATION RELATIONAL EXPRESSIONS FOR DIFFERENT OXYGEN CONCENTRATIONS AND DIFFERENT $NO_2$ CONCENTRATIONS

FIG. 4

SENSOR CONTROL METHOD AND SENSOR CONTROL APPARATUS

BACKGROUND OF THE INVENTION

Field of the Invention

The present invention relates to a sensor control method and a sensor control apparatus for controlling a sensor suitable for detection of the concentrations of nitrogen oxides and ammonia contained in a gas under measurement.

Description of Related Art

In recent years, a urea SCR (Selective Catalytic Reduction) system has drawn people's attention as a technique for purifying nitrogen oxides ($NO_x$) contained in exhaust gas discharged from an internal combustion engine such as a gasoline engine, a diesel engine, or the like. The urea SCR system is a system which chemically reacts ammonia ($NH_3$) with nitrogen oxides ($NO_x$) so as to reduce the nitrogen oxides to nitrogen ($N_2$), to thereby purify the nitrogen oxides contained in the exhaust gas.

This urea SCR system has a possibility that when the amount of ammonia supplied to nitrogen oxides becomes excessively large, unreacted ammonia is discharged to the outside in a state in which it is contained in the exhaust gas. In order to suppress discharge of such ammonia, a sensor which can measure the concentrations of a plurality of types of gases and which includes a sensor element for measuring the concentration of ammonia contained in exhaust gas is used for the urea SCR system.

In the urea SCR system, the amount of ammonia used for reduction of nitrogen oxides is adjusted such that the concentration of ammonia measured by the above-described sensor; i.e., the concentration of ammonia contained in exhaust gas, falls within a predetermined range.

Notably, an example of such a sensor is that which has an $NO_x$ sensor section and an ammonia sensor section. Also, examples of the configuration of such a sensor include a configuration in which an $NO_x$ sensor section and an ammonia sensor section are provided individually and a configuration in which an $NO_x$ sensor section and an ammonia sensor section are integrated together (multi-gas sensor). Nitrogen monoxide (NO), nitrogen dioxide ($NO_2$) and ammonia ($NH_3$) can be detected through use of such a sensor.

Also, detection of ammonia concentration by the ammonia sensor section involves a possibility that the ammonia concentration varies due to the influence of oxygen concentration and the accuracy in detecting the ammonia concentration decreases. Therefore, there has been proposed a technique for calculating corrected ammonia concentration on the basis of an output signal of the ammonia sensor section and oxygen concentration (for example, see Patent Document 1). Such a technique for calculating corrected ammonia concentration can reduce the influence of the oxygen concentration in a gas under measurement, to thereby suppress a decrease in the accuracy in detecting the ammonia concentration.

PRIOR ART DOCUMENT

Patent Document 1 is Japanese Patent Application Laid-Open (kokai) No. 2011-075546

BRIEF SUMMARY OF THE INVENTION

However, in the configuration in which corrected ammonia concentration is calculated on the basis of the output signal of the ammonia sensor section and oxygen concentration, even in a situation in which the actual ammonia concentration does not change, the corrected ammonia concentration varies when oxygen concentration varies sharply, whereby the accuracy in detecting the ammonia concentration may decrease.

For example, in the case of an actual internal combustion engine, since oxygen concentration changes moment by moment in accordance with the operating conditions, the reaction speed of the ammonia sensor section and a sensor for calculating the oxygen concentration or a predicted value are not necessarily in synchronism with a variation in the oxygen concentration.

In particular, in the case where an instantaneous change in oxygen concentration such as a rich spike occurs, if the followability of the value of oxygen concentration to a change in the output of the ammonia sensor section is poor, a large calculation error is highly likely to be produced, whereby the accuracy in detecting the ammonia concentration may decrease.

An object of the present invention is to provide a sensor control method and a sensor control apparatus which can suppress a decrease in the accuracy of detection of the concentration of ammonia contained in a gas under measurement when the detection is performed through use of a sensor which detects the concentrations of nitrogen oxides and ammonia contained in the gas under measurement.

A sensor control method according to one aspect of the present invention is a sensor control method for controlling a sensor which includes an $NO_x$ sensor section and an ammonia sensor section, the method comprising an oxygen concentration computation step, a corrected concentration computation step, an oxygen concentration change rate computation step, and an ammonia concentration setting step.

The $NO_x$ sensor section has a first pumping cell and a second pumping cell.

The first pumping cell pumps out oxygen contained in a gas under measurement introduced into a measurement chamber and pumps oxygen into the measurement chamber.

The second pumping cell is configured such that a second pumping current flows through the second pumping cell in accordance with the concentration of $NO_x$ contained in the gas under measurement whose oxygen concentration has been adjusted by the first pumping cell.

The ammonia sensor section is formed on an outer surface of the $NO_x$ sensor section and outputs an ammonia concentration signal representing the concentration of ammonia contained in the gas under measurement.

In the oxygen concentration computation step, the concentration of oxygen contained in the gas under measurement is computed on the basis of the first pumping current flowing through the first pumping cell.

In the corrected concentration computation step, a corrected ammonia concentration is computed on the basis of the oxygen concentration and the ammonia concentration signal output from the ammonia sensor section.

In the oxygen concentration change rate computation step, an oxygen concentration change rate which is the rate of change of the oxygen concentration with elapse of time is computed.

In the ammonia concentration setting step, when a predetermined correction permission condition is satisfied, the corrected ammonia concentration is set to a detection result of the ammonia concentration. Meanwhile, in the ammonia concentration setting step, when the correction permission condition is not satisfied, among the corrected ammonia concentrations computed in the past, the corrected ammonia concentration computed when the correction permission condition was satisfied is set to the detection result of the ammonia concentration. Notably, in the ammonia concentration setting step, when the oxygen concentration change rate is less than a predetermined reference judgment value, the correction permission condition is judged to be satisfied, and when the oxygen concentration change rate is equal to or greater than the reference judgment value, the correction permission condition is judged to be not satisfied.

In this sensor control method, in accordance with the result of the judgment as to whether or not the correction permission condition is satisfied, the setting operation is switched between an operation of setting the corrected ammonia concentration to the detection result of the ammonia concentration and an operation of setting the corrected ammonia concentration computed in the past (specifically, any one of corrected ammonia concentrations computed when the correction permission condition was satisfied) to the detection result of the ammonia concentration.

Notably, when the oxygen concentration change rate is less than the predetermined reference judgment value, it is judged that the correction permission condition is satisfied. Namely, the oxygen concentration change rate increases as the degree of steepness of the change in the oxygen concentration increases. Therefore, in the case where the oxygen concentration change rate is equal to or greater than the reference judgment value, it is possible to determine that the oxygen concentration changed sharply and judge that the correction permission condition is not satisfied. Notably, as the reference judgment value for the oxygen concentration change rate, there is previously set, for example, a boundary value between an oxygen concentration change rate which causes the ammonia concentration detection error to fall within an allowable range (±5%, preferably, ±3%) when the corrected ammonia concentration is computed and an oxygen concentration change rate which causes the ammonia concentration detection error to deviate from the allowable range.

Namely, in the case where the oxygen concentration change rate becomes less than the predetermined reference judgment value and satisfies the correction permission condition, the detection error of the ammonia concentration in the corrected ammonia concentration falls within the allowable range. Therefore, when the corrected ammonia concentration is set to the detection result of the ammonia concentration, the ammonia concentration detection accuracy does not decrease.

Meanwhile, in the case where the oxygen concentration change rate becomes equal to or greater than the reference judgment value and does not satisfy the correction permission condition, the detection error of the ammonia concentration in the corrected ammonia concentration falls outside the allowable range. Therefore, when the corrected ammonia concentration is set to the detection result of the ammonia concentration, the ammonia concentration detection accuracy decreases. Such a decrease in the ammonia concentration detection accuracy can be suppressed by setting, instead of such a corrected ammonia concentration, a past corrected ammonia concentration computed when the correction permission condition was satisfied to the detection result of the ammonia concentration.

Namely, in the case where the actual ammonia concentration did not change greatly and the oxygen concentration changed, it is considered that the past corrected ammonia concentration computed when the correction permission condition was satisfied has a value close to the actual ammonia concentration. Therefore, a decrease in the ammonia concentration detection accuracy can be suppressed by setting to the detection result of the ammonia concentration the past corrected ammonia concentration computed when the correction permission condition was satisfied.

Therefore, according to this sensor control method, when a sensor for detecting the concentrations of nitrogen oxides and ammonia contained in the gas under measurement is used, it is possible to suppress a decrease in the ammonia concentration detection accuracy.

In the above-described sensor control method, in the ammonia concentration setting step, when the correction permission condition is not satisfied, among the corrected ammonia concentrations computed in the past, the latest corrected ammonia concentration computed when the correction permission condition was satisfied may be set to the detection result of the ammonia concentration.

A decrease in the ammonia concentration detection accuracy can be suppressed by, as described above, setting to the detection result of the ammonia concentration the latest one of the past corrected ammonia concentrations computed when the correction permission condition was satisfied.

Namely, in the case where the actual ammonia concentration did not change greatly and the oxygen concentration changed, it is considered that the latest one of the past corrected ammonia concentrations computed when the correction permission condition was satisfied has a value close to the actual ammonia concentration.

Therefore, a decrease in the ammonia concentration detection accuracy can be suppressed by, as described above, setting the latest corrected ammonia concentration to the detection result of the ammonia concentration.

In the above-described sensor control method, in the ammonia concentration setting step, when the correction permission condition is not satisfied, the ammonia concentration set to the detection result of the last time may be set to the detection result of the ammonia concentration of this time.

Namely, since the numerical value set to the detection result of the ammonia concentration is the corrected ammonia concentration computed when the correction permission condition was satisfied, the ammonia concentration set to the detection result of the last time is also the corrected ammonia concentration computed when the correction permission condition was satisfied. Since the ammonia concentration set to the detection result of the last time is the latest corrected ammonia concentration among the past corrected ammonia concentrations computed when the correction permission condition was satisfied, the ammonia concentration set to the detection result of the last time assumes a value close to the actual ammonia concentration.

Therefore, a decrease in the ammonia concentration detection accuracy can be suppressed by, as described above, setting to the detection result of the ammonia concentration of this time the ammonia concentration set to the detection result of the last time.

In the above-described sensor control method, in the ammonia concentration setting step, when the oxygen concentration change rate is less than the reference judgment value and the oxygen concentration exceeds a predetermined reference concentration, the correction permission condition may be judged to be satisfied, and when at least one of a condition that the oxygen concentration change rate is equal to or greater than the reference judgment value and a condition that the oxygen concentration is equal to or less than the reference concentration is satisfied, the correction permission condition may be judged to be not satisfied.

In this sensor control method, the judgment as to whether or not the correction permission condition is satisfied is made on the basis of not only the oxygen concentration change rate but also the oxygen concentration so as to switch the setting operation between the operation of setting the corrected ammonia concentration to the detection result of the ammonia concentration and the operation of setting the corrected ammonia concentration computed in the past (specifically, the corrected ammonia concentration computed when the correction permission condition was satisfied) to the detection result of the ammonia concentration.

Notably, as to the oxygen concentration used for judging whether or not the correction permission condition is satisfied, a judgment is made as to whether or not the oxygen concentration exceeds a predetermined reference concentration. Namely, when the oxygen concentration becomes extremely low, the error of the corrected ammonia concentration tends to increase. Therefore, in the case where the oxygen concentration is equal to or less than the reference concentration, it is possible to determine that the error of the corrected ammonia concentration is large. Notably, as the reference concentration for the oxygen concentration, there is previously set, for example, a boundary value between an oxygen concentration which causes the ammonia concentration detection error to fall within the allowable range when the corrected ammonia concentration is computed and an oxygen concentration which causes the ammonia concentration detection error to deviate from the allowable range. For example, in the case where the reference concentration is set to 4%, it is judged that the correction permission condition is not satisfied at least when the oxygen concentration is 4% or less.

In this ammonia concentration setting step, when both of two conditions; i.e., a condition that "the oxygen concentration change rate is less than the reference judgment value" and a condition that "the oxygen concentration exceeds the reference concentration" are satisfied, it is judged that the correction permission condition is satisfied. Also, in this ammonia concentration setting step, when at least one of two conditions; i.e., a condition that "the oxygen concentration change rate is equal to or greater than the reference judgment value" and a condition that "the oxygen concentration is equal to or less than the reference concentration" is satisfied, it is judged that the correction permission condition is not satisfied.

Namely, in the case where the correction permission condition determined on the basis of the oxygen concentration and the oxygen concentration change rate is satisfied, the detection error of the ammonia concentration in the corrected ammonia concentration falls within the allowable range. Therefore, when the corrected ammonia concentration is set to the detection result of the ammonia concentration, it is possible to suppress a decrease in the ammonia concentration detection accuracy.

Meanwhile, in the case where the correction permission condition determined on the basis of the oxygen concentration and the oxygen concentration change rate is not satisfied, the ammonia concentration detection error in the corrected ammonia concentration falls outside the allowable range. Therefore, when the corrected ammonia concentration is set to the detection result of the ammonia concentration, the ammonia concentration detection accuracy decreases. Such a decrease in the ammonia concentration detection accuracy can be suppressed further by setting, instead of such corrected ammonia concentration, the past corrected ammonia concentrations computed when the correction permission condition was satisfied to the detection result of the ammonia concentration.

Namely, in the case where the actual ammonia concentration did not change greatly and the oxygen concentration changed, it is considered that the past corrected ammonia concentrations computed when the correction permission condition was satisfied has a value close to the actual ammonia concentration. Therefore, a decrease in the ammonia concentration detection accuracy can be suppressed further by setting the above-described corrected ammonia concentration to the detection result of the ammonia concentration.

Therefore, according to this sensor control method, when a sensor for detecting the concentrations of nitrogen oxides and ammonia contained in the gas under measurement is used, it is possible to further suppress a decrease in the ammonia concentration detection accuracy by judging whether or not the correction permission condition is satisfied on the basis of not only the oxygen concentration change rate but also the oxygen concentration.

In the above-described sensor control method, in the ammonia concentration setting step, the correction permission condition may be judged to be not satisfied, until a predetermined stop period elapses after the correction permission condition has been judged to be not satisfied.

Namely, when it is judged that the correction permission condition is not satisfied, there is a high possibility that, during a certain period after that, the influence of the oxygen concentration remains and the corrected ammonia concentration has an error.

In view of this, until the stop period elapses after it has been judged that the correction permission condition is not satisfied, it is judged that the correction permission condition is not satisfied. Thus, among the corrected ammonia concentrations computed in the past, a corrected ammonia concentration computed when the correction permission condition was satisfied is set to the detection result of the ammonia concentration.

As a result, it is possible to avoid a corrected ammonia concentration which is highly likely to involve an error from being set to the detection result of the ammonia concentration. Therefore, according to this sensor control method, a decrease in the ammonia concentration detection accuracy can be suppressed further.

In the above-described sensor control method, in the oxygen concentration change rate computation step, the oxygen concentration change rate may be computed by dividing the oxygen concentration computed last time by the oxygen concentration computed this time.

Namely, in computation of the oxygen concentration change rate, a value obtained by dividing the oxygen concentration computed last time by the oxygen concentration computed this time is computed as the oxygen concentration change rate. As a result, when the oxygen concentration decreases, the oxygen concentration change rate assumes a large value. Therefore, the oxygen concentration change rate changes greatly as a result of a small change in the oxygen concentration, whereby the judgment as to whether or not the oxygen concentration change rate has changed can be made easily.

Therefore, according to this sensor control method, it is possible to improve the accuracy of the judgment based on the oxygen concentration change rate, to thereby suppress a decrease in the ammonia concentration detection accuracy to a greater degree.

In the above-described sensor control method, the sensor may be a multi-gas sensor which includes the $NO_x$ sensor section and the ammonia sensor section integrated together.

Since such a multi-gas sensor includes the $NO_x$ sensor section and the ammonia sensor section integrated together, it is used for an application of detecting the concentrations of nitrogen oxides and ammonia contained in the same gas under measurement.

Therefore, according to this sensor control method, when a multi-gas sensor for detecting the concentrations of nitrogen oxides and ammonia contained in the gas under measurement is used, it is possible to suppress a decrease in the ammonia concentration detection accuracy.

In the above-described sensor control method, the sensor may include the $NO_x$ sensor section and the ammonia sensor section separately provided therein and be disposed in an exhaust path of an internal combustion engine. The exhaust path may include a plurality of spaces separated from one another by partition portions through which exhaust gas can pass. The $NO_x$ sensor section and the ammonia sensor section may be disposed in the same space among the plurality of spaces.

Since such a sensor is configured such that the $NO_x$ sensor and the ammonia sensor are disposed in the same space of the exhaust path, it is possible to detect the concentrations of nitrogen oxides and ammonia contained in the gas under measurement in the same space.

Therefore, according to this sensor control method, when a sensor for detecting the concentrations of nitrogen oxides and ammonia contained in the gas under measurement in the same space is used, it is possible to suppress a decrease in the ammonia concentration detection accuracy.

In the above-described sensor control method in which the $NO_x$ sensor section and the ammonia sensor section are provided separately, the $NO_x$ sensor section may be disposed at the same position as the ammonia sensor section or on the upstream side of the ammonia sensor section in a flow direction of the exhaust gas.

Since the relative positional relationship between the $NO_x$ sensor and the ammonia sensor is determined in this manner, the oxygen concentration detection position is located at the same position as the ammonia concentration detection position or on the upstream side of the ammonia concentration detection position in the flow direction of the exhaust gas. In this case, in computation of the corrected ammonia concentration, the oxygen concentration detected at the same position as the ammonia concentration detection position or on the upstream side of the ammonia concentration detection position can be used. As a result, the detection timing of the oxygen concentration does not fall behind the detection timing of the ammonia concentration, and the corrected ammonia concentration can be computed accurately.

Therefore, according to this sensor control method, the corrected ammonia concentration can computed accurately, whereby a decrease in the ammonia concentration detection accuracy can be suppressed.

A sensor control apparatus according to another aspect of the present invention is a sensor control apparatus for controlling a sensor which includes an $NO_x$ sensor section and an ammonia sensor section, the apparatus comprising an oxygen concentration computation section, a corrected concentration computation section, an oxygen concentration change rate computation section, and an ammonia concentration setting section.

The $NO_x$ sensor section has a first pumping cell and a second pumping cell.

The first pumping cell pumps out oxygen contained in a gas under measurement introduced into a measurement chamber and pumps oxygen into the measurement chamber.

The second pumping cell is configured such that a second pumping current flows through the second pumping cell in accordance with the concentration of $NO_x$ contained in the gas under measurement whose oxygen concentration has been adjusted by the first pumping cell.

The ammonia sensor section is formed on an outer surface of the $NO_x$ sensor section and outputs an ammonia concentration signal representing the concentration of ammonia contained in the gas under measurement.

The oxygen concentration computation section computes the concentration of oxygen contained in the gas under measurement on the basis of the first pumping current flowing through the first pumping cell.

The corrected concentration computation section computes a corrected ammonia concentration on the basis of the oxygen concentration and the ammonia concentration signal output from the ammonia sensor section.

The oxygen concentration change rate computation section computes an oxygen concentration change rate which is the rate of change of the oxygen concentration with elapse of time.

When a predetermined correction permission condition is satisfied, the ammonia concentration setting section sets the corrected ammonia concentration to a detection result of the ammonia concentration. Meanwhile, when the correction permission condition is not satisfied, the ammonia concentration setting section sets to the detection result of the ammonia concentration the corrected ammonia concentration computed when the correction permission condition was satisfied, among the corrected ammonia concentrations computed in the past. Notably, when the oxygen concentration change rate is less than a predetermined reference judgment value, the ammonia concentration setting section judges that the correction permission condition is satisfied, and when the oxygen concentration change rate is equal to or greater than the reference judgment value, the ammonia concentration setting section judges that the correction permission condition is not satisfied.

Like the above-described sensor control method, this sensor control apparatus can suppress a decrease in the ammonia concentration detection accuracy when a multi-gas sensor for detecting the concentrations of nitrogen oxides and ammonia contained in the gas under measurement is used.

In the above-described sensor control apparatus, when the correction permission condition is not satisfied, the ammonia concentration setting section may set to the detection result of the ammonia concentration the latest corrected ammonia concentration computed when the correction permission condition was satisfied, among the corrected ammonia concentrations computed in the past.

Like the above-described sensor control method, this sensor control apparatus can suppress a decrease in the ammonia concentration detection accuracy by setting the latest corrected ammonia concentration to the detection result of the ammonia concentration.

In the above-described sensor control apparatus, when the correction permission condition is not satisfied, the ammonia concentration setting section may set to the detection result of the ammonia concentration of this time the ammonia concentration set to the detection result of the last time.

Like the above-described sensor control method, this sensor control apparatus can suppress a decrease in the ammonia concentration detection accuracy by setting to the detection result of the ammonia concentration of this time the ammonia concentration set to the detection result of the last time.

In the above-described sensor control apparatus, when the oxygen concentration change rate is less than the reference judgment value and the oxygen concentration exceeds a predetermined reference concentration, the ammonia concentration setting section may judge that the correction permission condition is satisfied, and when at least one of a condition that the oxygen concentration change rate is equal to or greater than the reference judgment value and a condition that the oxygen concentration is equal to or less than the reference concentration is satisfied, the ammonia concentration setting section may judge that the correction permission condition is not satisfied.

Like the above-described sensor control method, this sensor control apparatus can further suppress a decrease in the ammonia concentration detection accuracy by judging whether or not the correction permission condition is satisfied on the basis of not only the oxygen concentration change rate but also the oxygen concentration when a sensor for detecting the concentrations of nitrogen oxides and ammonia contained in the gas under measurement is used.

In the above-described sensor control apparatus, the sensor may be a multi-gas sensor which includes the $NO_x$ sensor section and the ammonia sensor section integrated together.

Since such a multi-gas sensor includes the $NO_x$ sensor section and the ammonia sensor section integrated together, it is used for an application of detecting the concentrations of nitrogen oxides and ammonia contained in the same gas under measurement.

Therefore, according to this sensor control apparatus, when a multi-gas sensor for detecting the concentrations of nitrogen oxides and ammonia contained in the gas under measurement is used, it is possible to suppress a decrease in the ammonia concentration detection accuracy.

In the above-described sensor control apparatus, the sensor may include the $NO_x$ sensor section and the ammonia sensor section separately provided therein and be disposed in an exhaust path of an internal combustion engine. The exhaust path may include a plurality of spaces separated from one another by partition portions through which exhaust gas can pass. The $NO_x$ sensor section and the ammonia sensor section may be disposed in the same space among the plurality of spaces.

Since such a sensor is configured such that the $NO_x$ sensor and the ammonia sensor are disposed in the same space of the exhaust path, it is possible to detect the concentrations of nitrogen oxides and ammonia contained in the gas under measurement in the same space.

Therefore, according to this sensor control apparatus, when a sensor for detecting the concentrations of nitrogen oxides and ammonia contained in the gas under measurement in the same space is used, it is possible to suppress a decrease in the ammonia concentration detection accuracy.

In the above-described sensor control apparatus in which the $NO_x$ sensor section and the ammonia sensor section are provided separately, the $NO_x$ sensor section may be disposed at the same position as the ammonia sensor section or on the upstream side of the ammonia sensor section in a flow direction of the exhaust gas.

Since the relative positional relationship between the $NO_x$ sensor and the ammonia sensor is determined in this manner, the oxygen concentration detection position is located at the same position as the ammonia concentration detection position or on the upstream side of the ammonia concentration detection position in the flow direction of the exhaust gas. In this case, in computation of the corrected ammonia concentration, the oxygen concentration detected at the same position as the ammonia concentration detection position or on the upstream side of the ammonia concentration detection position can be used. As a result, the detection timing of the oxygen concentration does not fall behind the detection timing of the ammonia concentration, and the corrected ammonia concentration can be computed accurately.

Therefore, according to this sensor control apparatus, the corrected ammonia concentration can computed accurately, whereby a decrease in the ammonia concentration detection accuracy can be suppressed.

According to the sensor control method and the sensor control apparatus of the present invention, when a sensor for detecting the concentrations of nitrogen oxides and ammonia contained in a gas under measurement is used, it is possible to suppress a decrease in the ammonia concentration detection accuracy.

BRIEF DESCRIPTION OF THE DRAWINGS

FIG. 4 is a block diagram showing the configuration of various types of data stored in a microcomputer of the multi-gas sensor control apparatus.

DETAILED DESCRIPTION OF EXEMPLARY EMBODIMENTS OF THE INVENTION

Embodiments to which the present invention is applied will be described with reference to the drawings.

Notably, needles to say, the present invention is not limited to the following embodiments, and various forms may be employed so long as they fall within the technical scope of the present invention.

1. First Embodiment 1-1. Overall Configuration

A multi-gas sensor control apparatus 1 provided for an internal combustion engine of an automobile or the like will be described as a first embodiment.

The multi-gas sensor control apparatus 1 is used for a urea SCR system which purifies nitrogen oxides ($NO_x$) contained in exhaust gas (gas under measurement) discharged from a diesel engine. More specifically, the multi-gas sensor control apparatus 1 measures the concentrations of nitrogen monoxide (NO), nitrogen dioxide ($NO_2$), and ammonia contained in exhaust gas after having undergone the reaction between ammonia (urea) and $NO_x$ contained in the exhaust gas.

Figure 1:
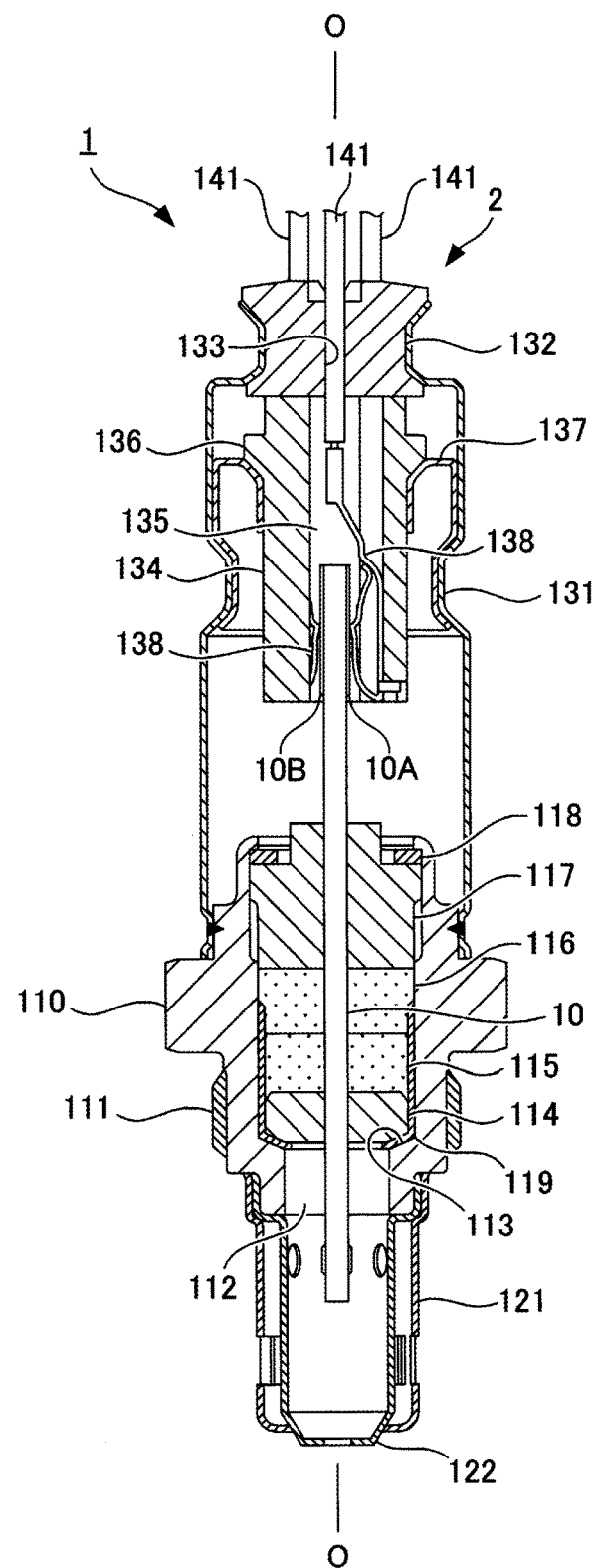
FIG. 1 is a sectional view showing the internal structure of a multi-gas sensor provided in a multi-gas sensor control apparatus.
Figure 2:
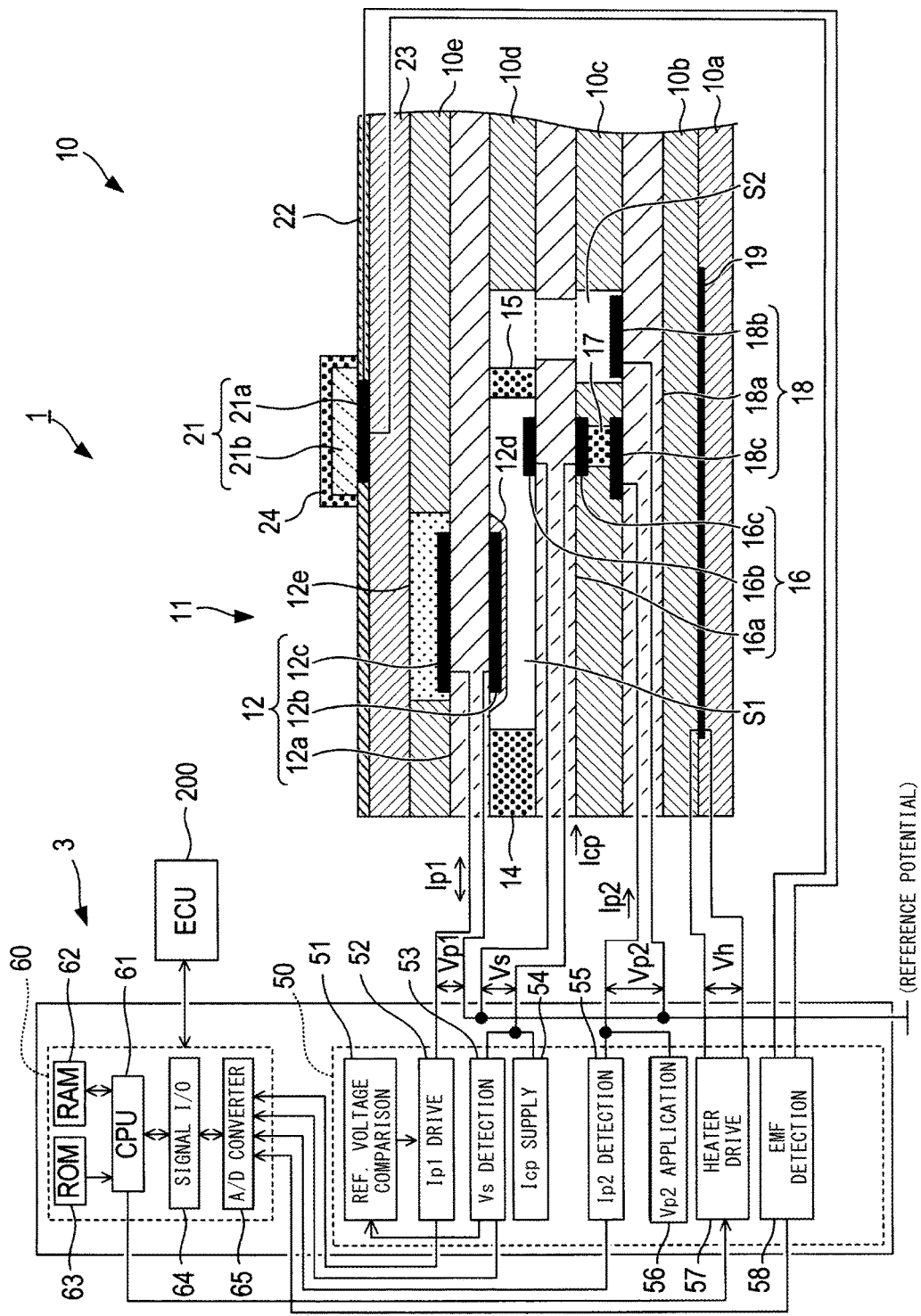
FIG. 2 is a block diagram describing the configuration of the multi-gas sensor control apparatus.

As shown in FIGS. 1 and 2, the multi-gas sensor control apparatus 1 includes a multi-gas sensor 2 which is a sensor main body and a control section 3 (computation section 3) which controls the multi-gas sensor 2 and processes the sensor outputs to thereby compute the concentrations of NO, $NO_2$, and ammonia.

1-2. Multi-Gas Sensor

As shown in FIG. 1, the multi-gas sensor 2 mainly includes a sensor element section 10, a metallic shell 110, a separator 134, and connection terminals 138. Notably, in the following description, the side (the lower side of FIG. 1) where the sensor element section 10 of the multi-gas sensor 2 is disposed will be referred to as a forward end side, and the side (the upper side of FIG. 1) where the connection terminals 138 are disposed will be referred to as a rear end side.

The sensor element section 10 has the shape of a plate extending in the direction of an axis O. Electrode terminal portions 10A and 10B are disposed at the rear end of the sensor element section 10. In FIG. 1, in order to facilitate the illustration, only the electrode terminal portions 10A and 10B are shown as the electrode terminal portions formed on the sensor element section 10. However, in actuality, a plurality of electrode terminal portions are formed in accordance with the number of the electrodes of an $NO_x$ sensor section 11 and an ammonia sensor section 21 which will be described later and other electrodes. Notably, the sensor element section 10 will be described in detail later.

The metallic shell 110 is a tubular member which has a screw portion 111 formed on the outer surface thereof and used for fixing the multi-gas sensor 2 to an exhaust pipe of the diesel engine. The metallic shell 110 mainly has a through hole 112 penetrating therethrough in the axial direction and a ledge portion 113 projecting inward in the radial direction of the through hole 112. The ledge portion 113 has an inward-facing taper surface inclined such that it approaches the forward end side as approaching from the outer side toward the center in the radial direction of the through hole 112.

Also, the metallic shell 110 holds the sensor element section 10 in a state in which a forward end portion of the sensor element section 10 projects toward the forward end side of the through hole 112 and a rear end portion of the sensor element section 10 projects toward the rear end side of the through hole 112.

A ceramic holder 114 which is a tubular member surrounding the radial circumference of the sensor element section 10, talc rings 115 and 116 which are powder charged layers, and a ceramic sleeve 117 are stacked in the through hole 112 of the metallic shell 110 in this order from the forward end side toward the rear end side.

A crimp packing 118 is disposed between the ceramic sleeve 117 and an end portion of the metallic shell 110 on the rear end side. A metallic holder 119 is disposed between the ceramic holder 114 and the ledge portion 113 of the metallic shell 110. The metallic holder 119 holds the talc ring 115 and the ceramic holder 114. An end portion of the metallic shell 110 on the rear end side is a portion crimped such that it presses the ceramic sleeve 117 toward the forward end side through a crimp packing 118.

An outer protector 121 and an inner protector 122 are provided at the end portion of the metallic shell 110 on the forward end side. Each of the outer protector 121 and the inner protector 122 is a tubular member which is formed of a metallic material such as stainless steel and which is closed at the end on the forward end side. The inner protector 122 is welded to the metallic shell 110 in a state in which it covers the forward-end-side end portion of the sensor element section 10. The outer protector 121 is welded to the metallic shell 110 in a state in which it covers the inner protector 122.

A forward-end-side end portion of an outer tube 131 formed into a tubular shape is fixed to the rear-end-side end portion of the metallic shell 110. Further, a grommet 132 is disposed in an opening at a rear-end side end portion of the outer tube 131 so as to close the opening.

The grommet 132 has lead wire passage holes 133 through which lead wires 141 are passed. The lead wires 141 are electrically connected to the electrode terminal portion 10A and the electrode terminal portion 10B of the sensor element section 10.

The separator 134 is a tubular member disposed on the rear end side of the sensor element section 10. A space formed in the separator 134 is a passage hole 135 which penetrates the separator 134 in the axial direction. A flange portion 136 projecting outward in the radial direction is formed on the outer surface of the separator 134.

A rear end portion of the sensor element section 10 is inserted into the passage hole 135 of the separator 134, and the electrode terminal portions 10A and 10B are disposed inside the separator 134.

A tubular holding member 137 is disposed between the separator 134 and the outer tube 131. The holding member 137 comes into contact with the flange portion 136 of the separator 134 and comes into contact with the inner surface of the outer tube 131 to thereby fix and hold the separator 134 to the outer tube 131.

The connection members 138 are electrically conductive members which are disposed in the passage hole 135 of the separator 134 and which individually and electrically connect the lead wires 141 to the electrode terminal portion 10A and the electrode terminal portion 10B of the sensor element section 10. Notably, in FIG. 1, in order to facilitate the illustration, only two of the connection members 138 are shown.

1-3. Sensor Element Section

Here, the structure of the sensor element section 10 will be described in detail with reference to FIG. 2. Notably, for convenience of description, FIG. 2 shows only a schematic sectional view of the sensor element section 10 along the longitudinal direction thereof.

The $NO_x$ sensor section 11 and the ammonia sensor section 21 are mainly provided in the sensor element section 10. The $NO_x$ sensor section 11 and the ammonia sensor section 21 in the present embodiment have structures similar to those of a known $NO_x$ sensor and a known ammonia sensor.

The $NO_x$ sensor section 11 has a structure in which mainly an insulating layer 10e, a first solid electrolyte member 12a, an insulating layer 10d, a third solid electrolyte member 16a, an insulating layer 10c, a second solid electrolyte member 18a, an insulating layer 10b, and an insulating layer 10a are stacked in this order. The insulating layers 10a, 10b, 10c, 10d, and 10e are mainly formed of alumina.

Further, in the $NO_x$ sensor section 11, a first measurement chamber S1 is provided between the first solid electrolyte member 12a and the third solid electrolyte member 16a, and a second measurement chamber S2 corresponding to an $NO_x$ measurement chamber is disposed between the first solid electrolyte member 12a and the second solid electrolyte member 18a such that the second measurement chamber S2 extends through the third solid electrolyte member 16a.

A first diffusion resistor 14 is disposed at the inlet end (the end on the left side of FIG. 2) of the first measurement chamber S1 into which a gas under measurement is introduced. A second diffusion resistor 15 which separates the first measurement chamber S1 and the second measurement chamber S2 from each other is disposed at the end (the end on the right side of FIG. 2) of the first measurement chamber S1 opposite to the inlet end. The above-described first and second diffusion resistor 14 and 15 are formed of a porous material such as alumina and are permeable to the gas under measurement.

Further, in the $NO_x$ sensor section 11, a heater (heater section) 19 is provided so as to heat the $NO_x$ sensor section 11 and the ammonia sensor section 21 to an activation temperature to thereby increase the oxygen-ion conductivity of the solid electrolyte members which constitute these sensors. The heater 19 is formed of platinum or an alloy containing platinum and has the shape of an elongated plate extending along the longitudinal direction of the sensor element section 10. The heater 19 is disposed between the insulating layer 10b and the insulating layer 10a.

Moreover, a first pumping cell 12, an oxygen concentration detection cell 16, and a second pumping cell 18 are provided in the $NO_x$ sensor section 11.

The first pumping cell 12 is mainly composed of a first solid electrolyte member 12a mainly formed of zirconia having oxygen-ion conductivity, and an inner first pumping electrode (first electrode) 12b and an outer first pumping electrode (first electrode) 12c which are mainly formed of platinum.

The inner first pumping electrode 12b is provided on a surface of the first solid electrolyte member 12a which is exposed to the first measurement chamber S1. Further, a surface of the inner first pumping electrode 12b on the side toward the first measurement chamber S1 is covered with a protection layer 12d formed of a porous material.

The outer first pumping electrode 12c is an electrode which serves as a counterpart of the inner first pumping electrode 12b, and is disposed such that the first solid electrolyte member 12a is sandwiched between the outer first pumping electrode 12c and the inner first pumping electrode 12b. A portion of the insulating layer 10e which corresponds to a region where the outer first pumping electrode 12c is disposed is cut away, and a porous member 12e is charged into the resultant space. The porous member 12e allows gas (oxygen) to flow between the outer first pumping electrode 12c and the outside.

The oxygen concentration detection cell 16 is disposed on the downstream side of the first pumping cell 12 and on the upstream side of the second pumping cell 18. The oxygen concentration detection cell 16 is mainly composed of a third solid electrolyte member 16a mainly formed of zirconia, and a detection electrode 16b and a reference electrode 16c which are mainly formed of platinum and which are disposed such that the third solid electrolyte member 16a is sandwiched therebetween.

The detection electrode 16b is formed on a surface of the third solid electrolyte member 16a which is exposed to the first measurement chamber S1 such that the detection electrode 16b is located on the downstream side of the inner first pumping electrode 12b; i.e., in a region near the second diffusion resistor 15.

The reference electrode 16c which is the counterpart of the detection electrode 16b is disposed in a reference oxygen chamber 17 formed by cutting away a portion of the insulating layer 10c. A porous member is charged into the reference oxygen chamber 17. Oxygen fed from the first measurement chamber S1 is present in the reference oxygen chamber 17, and the oxygen within the reference oxygen chamber 17 serves an oxygen reference.

The second pumping cell 18 is mainly composed of a second solid electrolyte member 18a mainly formed of zirconia, and an inner second pumping electrode (second electrode) 18b and a second pumping counterpart electrode (second electrode) 18c which are mainly formed of platinum.

The inner second pumping electrode 18b is formed in a region of the second solid electrolyte member 18a which is exposed to the second measurement chamber S2. The second pumping counterpart electrode 18c is formed in a region of the second solid electrolyte member 18a which is exposed to the reference oxygen chamber 17 such that the second pumping counterpart electrode 18c faces the reference electrode 16c.

Further, the above-described inner first pumping electrode 12b, detection electrode 16b, and inner second pumping electrode 18b are connected to a reference potential.

Meanwhile, the ammonia sensor section 21 is formed on the outer surface of the $NO_x$ sensor section 11; more specifically, on the insulating layer 10e. The ammonia sensor section 21 is disposed at approximately the same position as the reference electrode 16c in the longitudinal direction of the $NO_x$ sensor section 11 (the left-right direction of FIG. 2).

The ammonia sensor section 21 includes a pair of electrodes 21a formed on a solid electrolyte member 23 for the ammonia sensor section and a selective reaction layer 21b which covers the pair of electrodes 21a, and is configured to detect the concentration of ammonia contained in the gas under measurement from a change in the electromotive force between the pair of electrodes 21a.

Also, a diffusion layer 24 (protection layer 24) made of a porous material is formed to completely cover the selective reaction layer 21b. The diffusion layer 24 can adjust the diffusion speed of the gas under measurement which flows into the ammonia sensor section 21 from the outside.

Figure 3:
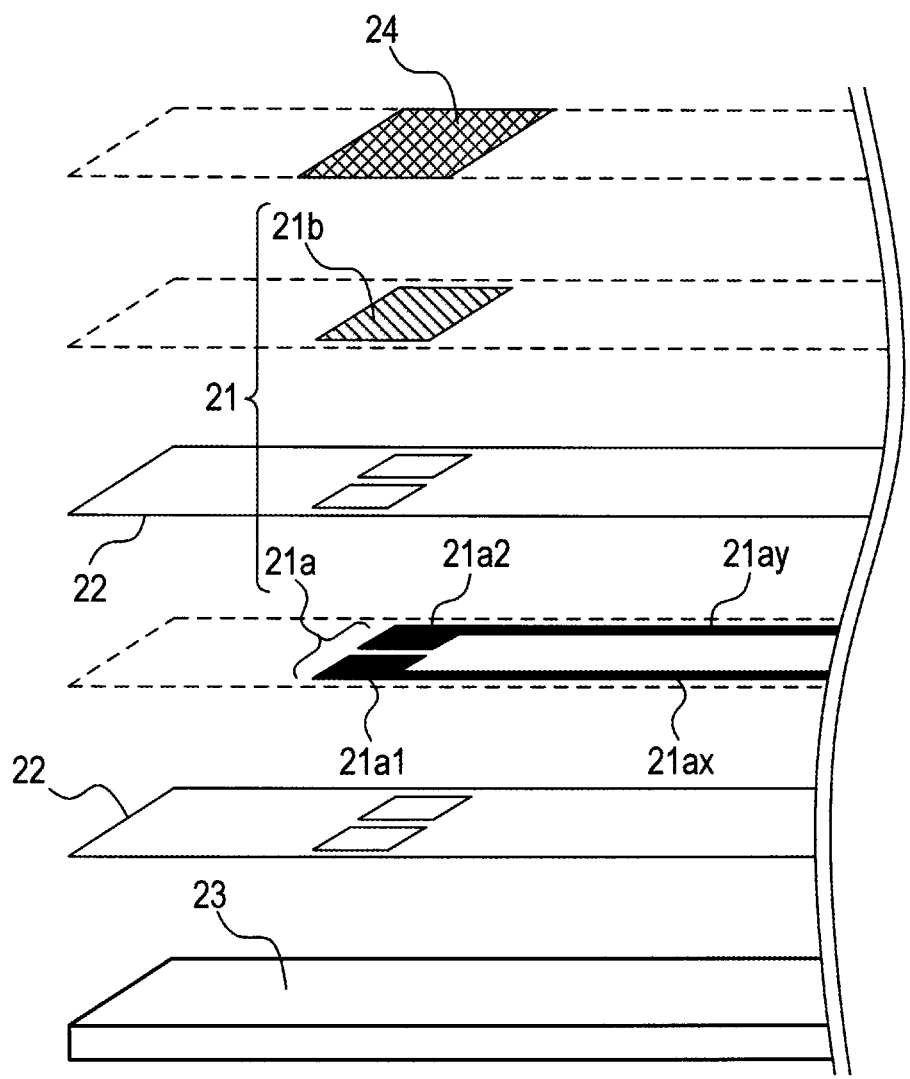
FIG. 3 is an exploded view showing the structure of an ammonia sensor section.

FIG. 3 is an exploded view showing the structure of the ammonia sensor section 21.

The pair of electrodes 21a are constituted by a pair of electrodes 21a1 and 21a2 disposed on the solid electrolyte member 23 for the ammonia sensor section.

Leads 21ax and 21ay extend from the electrodes 21a1 and 21a2 along the longitudinal direction of the solid electrolyte member 23 for the ammonia sensor section. The leads 21ax and 21ay are covered with an insulating layer 22. However, the right ends (not shown) of the leads 21ax and 2ay are not covered with the insulating layer 22 and are exposed, and form predetermined electrode terminal portions, respectively.

The electrodes 21a1 and 21a2 are juxtaposed along the lateral direction of the solid electrolyte member 23 for the ammonia sensor section such that they are spaced from each other. The electrode 21a1 is formed of a material which contains gold as a main component, and acts as a detection electrode. The electrode 21a2 is formed of a material which contains platinum as a main component, and acts as a reference electrode. Since the detection electrode 21a1 has a higher reactivity with ammonia as compared with the reference electrode 21a2, an electromotive force is produced between the detection electrode 21a1 and the reference electrode 21a2.

Also, the solid electrolyte member 23 for the ammonia sensor section is formed of, for example, an oxygen-ion conductive material such as $ZrO_2$, and the leads 21ax and 21ay are formed of, for example, a material which contains platinum as a main component.

The selective reaction layer 21b plays a role of burning combustible gas components (other than ammonia) contained in the gas under measurement. Since the selective reaction layer 21b is present, ammonia contained in the gas under measurement can be detected without receiving the influence of the combustible gas components. In general, the selective reaction layer 21b contains a metal oxide as a main components. However, the selective reaction layer 21b may be formed of a material which contains in particular vanadium oxide ($V_2O_5$) and bismuth oxide ($Bi_2O_3$) at a predetermined ratio (for example, vanadium-bismuth oxide: $BiVO_4$).

Notably, even in the case where the selective reaction layer 21b covers the detection electrode 21a1 only, it can exhibit the above-described effect. Also, in the present embodiment, the detection electrode 21a1 and the selective reaction layer 21b are provided separately. However, the embodiment may be modified by omitting the selective reaction layer 21b and adding to the detection electrode 21a1 a material (for example, a metal oxide) used to form the selective reaction layer 21b.

The diffusion layer 24 is formed of, for example, at least one material selected from the group consisting of alumina, spinel ($MgAl_2O_4$), silica alumina, and mullite. The gas diffusion time required to reach the selective reaction layer 21b and the electrodes 21a1 and 21a2 can be freely adjusted by properly adjusting the thickness of the diffusion layer 24, particle size, particle size distribution, porosity, compounding ratio, etc.

In the present embodiment, the temperature of the oxygen concentration detection cell 16 is measured, and heating by the heater 19 is performed on the basis of the measured temperature. Notably, in the present embodiment, when the controlled temperature of the second solid electrolyte member 18a of the $NO_x$ sensor section 11 is 700° C., the temperature of the ammonia sensor section 21 is 650° C.

1-4. Control Section

As shown in FIG. 2, the control section 3 of the multi-gas sensor control apparatus 1 is electrically connected to an ECU 200 which is a vehicle-side controller of a vehicle on which the multi-gas sensor control apparatus 1 is mounted. The ECU 200 receives data representing the concentrations of NO, NO2, and ammonia contained in exhaust gas which are computed by the control section 3. On the basis of the received data, the ECU 200 executes processing of controlling the operation state of the diesel engine, and executes processing of purifying NOx accumulated in a catalyst.

As shown in FIG. 2, a microcomputer 60 and a control circuit 50 which is an analog circuit disposed on a circuit board are provided in the control section 3.

The microcomputer 60 controls the entirety of the control section 3. A CPU (central processing unit) 61, a RAM 62 and a ROM 63 which are storage means, a signal input/output section 64, an A/D converter 65, and a clock (not shown) are mainly provided in the microcomputer 60. The microcomputer 60 performs various types of processing operations by causing the CPU 61 to execute programs stored in the ROM 63 or the like in advance.

The control circuit 50 is mainly composed of a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, and an electromotive force detection circuit 58.

The Ip1 drive circuit 52 is electrically connected to the outer first pumping electrode 12c of the NOx sensor section 11. The Vs detection circuit 53 and the Icp supply circuit 54 are electrically connected to the reference electrode 16c. The Ip2 detection circuit 55 and the Vp2 application circuit 56 are electrically connected to the second pumping counterpart electrode 18c. The heater drive circuit 57 is electrically connected to the heater 19.

The electromotive force detection circuit 58 is electrically connected to the pair of electrodes 21a (the detection electrode 21a1 and the reference electrode 21a2) of the ammonia sensor section 21. The electromotive force detection circuit 58 detects an ammonia electromotive force EMF which is the electromotive force between the detection electrode 21a1 and the reference electrode 21a2 and outputs the ammonia electromotive force EMF to the microcomputer 60.

The Ip1 drive circuit 52 supplies a first pumping current Ip1 between the inner first pumping electrode 12b and the outer first pumping electrode 12c and detects the supplied first pumping current Ip1.

The Vs detection circuit 53 detects a voltage Vs between the detection electrode 16b and the reference electrode 16c and outputs the detected voltage Vs to the reference voltage comparison circuit 51. The reference voltage comparison circuit 51 compares a reference voltage (e.g., 425 mV) and the output (voltage Vs) of the Vs detection circuit 53 and outputs the result of the comparison to the Ip1 drive circuit 52.

The Ip1 drive circuit 52 controls the flow direction and magnitude of the Ip1 current such that the voltage Vs becomes equal to the above-described reference voltage, and adjusts the concentration of oxygen within the first measurement chamber S1 to a predetermined value at which NOx does not decompose.

The Icp supply circuit 54 causes a weak current Icp to flow between the detection electrode 16b and the reference electrode 16c. As a result of supply of the current Icp, oxygen is fed from the first measurement chamber S1 to the reference oxygen chamber 17, whereby the reference electrode 16c is exposed to a predetermined oxygen concentration serving as a reference.

The Vp2 application circuit 56 applies a constant voltage Vp2 (e.g., 450 mV) between the inner second pumping electrode 18b and the second pumping counterpart electrode 18c so as to decompose NOx to nitrogen and oxygen. The constant voltage Vp2 is a voltage at which the NOx gas contained in the gas under measurement decomposes to oxygen and N2 gas.

The Ip2 detection circuit 55 detects a second pumping current Ip2 flowing to the second pumping cell 18. The second pumping current Ip2 is a current which flows when oxygen produced as a result of decomposition of NOx is pumped out from the second measurement chamber S2 toward the second pumping counterpart electrode 18c through the second solid electrolyte member 18a.

The Ip1 drive circuit 52 outputs the detected value of the first pumping current Ip1 to the A/D converter 65, and the Ip2 detection circuit 55 outputs the detected value of the second pumping current Ip2 to the A/D converter 65. The A/D converter 65 converts the values of the first pumping current Ip1 and the second pumping current Ip2 to digital values and outputs the digital values to the CPU 61 via the signal input/output section 64.

1-5. Control Circuit

Next, control by the control circuit 50 will be described.

First, when the engine is started and electric power is supplied to the control circuit 50 from the outside, electric power is supplied from the heater drive circuit 57 to the heater 19. The heater 19 to which electric power is supplied generates heat, and heat the first pumping cell 12, the oxygen concentration detection cell 16, and the second pumping cell 18 to an activation temperature.

When the $NO_x$ sensor section 11 is heated to a target temperature by the heater 19, the ammonia sensor section 21 disposed on the $NO_x$ sensor section 11 is also heated to a desired temperature and is activated.

Further, the current Icp is supplied from the Icp supply circuit 54 so that the current Icp flows between the detection electrode 16b and the reference electrode 16c. As a result, oxygen is fed from the first measurement chamber S1 into the reference oxygen chamber 17, and the fed oxygen becomes an oxygen reference.

Once the first pumping cell 12, the oxygen concentration detection cell 16, and the second pumping cell 18 are heated to the activation temperature, the first pumping cell 12 pumps out oxygen within the first measurement chamber S1. Namely, oxygen contained in the gas under measurement (exhaust gas) having flowed into the first measurement chamber S1 is pumped out so that the oxygen flows from the inner first pumping electrode 12b of the first pumping cell 12 toward the outer first pumping electrode 12c thereof.

The oxygen concentration within the first measurement chamber S1 becomes a concentration corresponding to the voltage Vs between the electrodes of the oxygen concentration detection cell 16. The Ip1 drive circuit 52 controls the first pumping current Ip1 flowing to the first pumping cell 12 such that the voltage Vs between the electrodes becomes equal to the above-described reference voltage. As a result, the oxygen concentration within the first measurement chamber S1 is controlled to a level at which $NO_x$ does not decompose.

The gas under measurement whose oxygen concentration has been adjusted in the first measurement chamber S1 flows into the second measurement chamber S2. In the second measurement chamber S2, $NO_x$ contained in the gas under measurement is decomposed to nitrogen and oxygen. Namely, when the constant voltage Vp2 (e.g., 450 mV) is applied from the Vp2 application circuit 56 as the voltage between the electrodes of the second pumping cell 18, $NO_x$ is decomposed to nitrogen and oxygen. The constant voltage Vp2 is a voltage at which $NO_x$ contained in the gas under measurement is decomposed to oxygen and $N_2$ and is higher than the control voltage of the oxygen concentration detection cell 16.

Oxygen produced as a result of decomposition of $NO_x$ is pumped out from the second measurement chamber S2 by the second pumping cell 18. At that time, the second pumping current Ip2 is supplied to the second pumping cell 18 in order to pump out oxygen. Since the second pumping current Ip2 and the $NO_x$ concentration have a direct proportional relationship therebetween, the second pumping current Ip2 detected by the Ip2 detection circuit 55 assumes a value which is direct proportional to the $NO_x$ concentration.

Meanwhile, an electromotive force is produced between the detection electrode 21a1 and the reference electrode 21a2 of the ammonia sensor section 21 in accordance with the concentration of ammonia contained in the gas under measurement. The electromotive force detection circuit 58 detects the electromotive force between the detection electrode 21a1 and the reference electrode 21a2 as an ammonia electromotive force.

Notably, the value of the second pumping current Ip2 involves the influences of the oxygen concentration, $NO_2$ concentration, and ammonia concentration of the gas under measurement within the second measurement chamber S2. Also, the ammonia electromotive force EMF output from the ammonia sensor section 21 involves the influences of the oxygen concentration, NO concentration, and $NO_2$ concentration of the gas under measurement, and the temperatures of the sensor sections 11 and 21. In the present embodiment, after the influence of the oxygen concentration is removed from the second pumping current Ip2 and the ammonia electromotive force, the NO concentration, the $NO_2$ concentration, and the ammonia concentration are obtained through computation processing. Notably, the details of the computation processing will be described later. Also, the oxygen concentration is that obtained from the first pumping current Ip1 by using a relational expression.

1-6. Microcomputer

Various types of data which will be described below are stored in the ROM 63 of the microcomputer 60. The CPU 61 reads the various types of data from in the ROM 63 and performs various types of computation processing such as removing the influence of the oxygen concentration from the value of the second pumping current Ip2 and the ammonia electromotive force.

As schematically shown in FIG. 4, the ROM 63 stores a "first pumping current (Ip1)—oxygen concentration relational expression" 63a, a plurality of "ammonia concentration output (electromotive force EMF)—ammonia concentration relational expressions" 63b set for different oxygen concentrations, a plurality of "second pumping current (Ip2)—NO concentration relational expressions" 63c set for different ammonia concentrations, an "negative ammonia concentration output—$NO_2$ concentration relational expression" 63d, a "contributive second pumping current—NO concentration, $NO_2$ concentration relational expression" 63e, and a plurality of "ammonia concentration output—ammonia concentration relational expressions" 63f set for different oxygen concentrations and different $NO_2$ concentrations.

Notably, in the example of FIG. 4, the various types of data 63a to 63f are set as predetermined relational expressions. However, the various types of data 63a to 63f may be, for example, tables which allow calculation of various types of gas concentrations from the output of the sensor. Also, the various types of data 63a to 63f may be values (relational expressions, tables, etc.) obtained through use of, for example, model gases whose gas concentrations are known.

The "first pumping current—oxygen concentration relational expression" 63a is a relational expression which represents the relation between the concentration of oxygen contained in the gas under measurement introduced into the first measurement chamber and the first pumping current (Ip1) flowing through the first pumping cell 12 as a result of pumping out of oxygen contained in the gas under measurement or pumping in of oxygen. Although not shown, in general, an approximately linear relation is present between the first pumping current Ip1 and the oxygen concentration. The concentration of oxygen contained in the gas under measurement can be calculated on the basis of the "first pumping current—oxygen concentration relational expression" 63a.

The "ammonia concentration output—ammonia concentration relational expression" 63b is set for each of different oxygen concentrations and is a relational expression between the ammonia concentration output of the ammonia sensor section and the concentration of ammonia contained in the gas under measurement.

Figure 5:
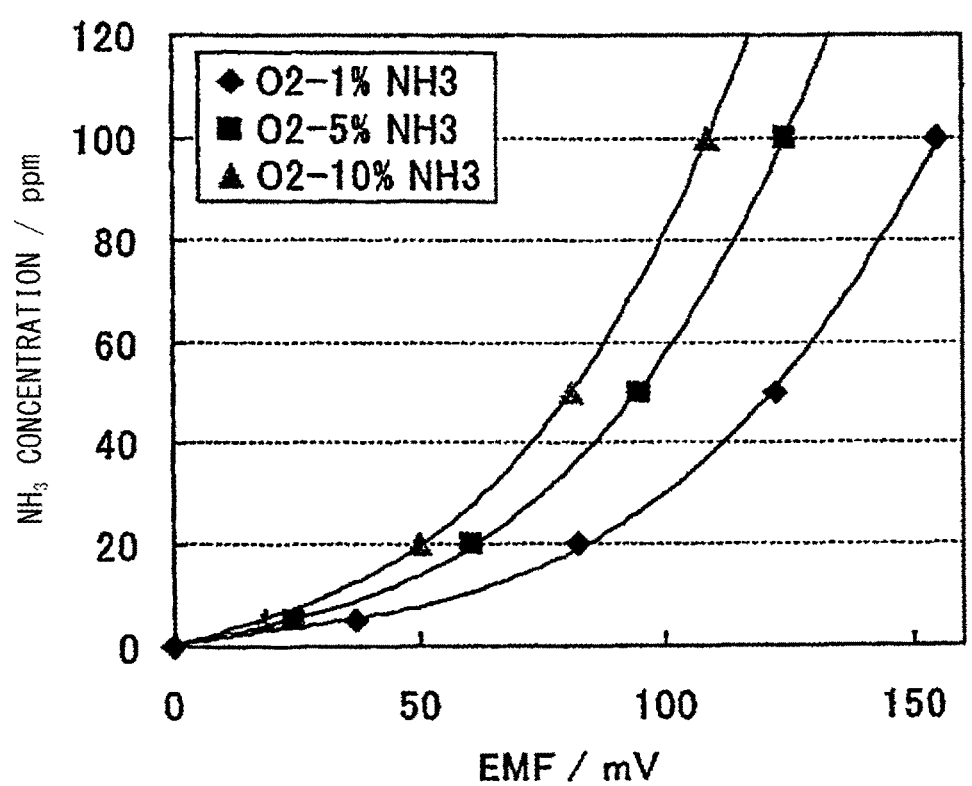
FIG. 5 is an explanatory graph showing an example of an ammonia concentration output—ammonia concentration relational expression.

FIG. 5 shows an example of the ammonia concentration output—ammonia concentration relational expression. In the present embodiment, for each of different oxygen concentrations, the ammonia concentration is represented by a cubic expression of EMF. Although EMF changes with the oxygen concentration, on the basis of the "ammonia concentration output—ammonia concentration relational expression" 63b for each oxygen concentration, accurate ammonia concentration ("corrected ammonia concentration" of claims) which is free from the influence of the concentration of oxygen contained in the gas under measurement can be computed.

Notably, the ammonia concentration output—ammonia concentration relational expression for a certain oxygen concentration which is not set can be obtained, through extrapolation, from the ammonia concentration output—ammonia concentration relational expressions for two oxygen concentrations which sandwich the certain oxygen concentration.

Also, the microcomputer 60 computes the NO concentration and the $NO_2$ concentration by using the "second pumping current (Ip2)—NO concentration relational expression" 63c, the "negative ammonia concentration output—$NO_2$ concentration relational expression" 63d, the "contributive second pumping current—NO concentration, $NO_2$ concentration relational expression" 63e, and the "ammonia concentration output—ammonia concentration relational expression" 63f.

Notably, known methods for computing the NO concentration and the $NO_2$ concentration are described in, for example, Japanese Patent Application Laid-Open (kokai) No. 2011-075546. Therefore, the detailed descriptions of the methods are not provided herein.

Next, there will be described the gas concentration computation processing executed by the CPU 61 of the microcomputer 60. The gas concentration computation processing is processing of computing the concentrations of various types of gas components of the gas under measurement (the NO concentration, the $NO_2$ concentration, and the ammonia concentration) by using the second pumping current Ip2 and the ammonia electromotive force EMF.

Notably, in the urea SCR system, in order to purify $NO_x$, urea water is injected in accordance with the detection result of the multi-gas sensor 2. When $NO_x$ is judged to have been purified, the injection of urea water is stopped. Accordingly, when a predetermined time has elapsed after the injection of urea water was stopped, the CPU 61 judges that "the ammonia concentration of the gas under measurement is zero."

Figure 6:
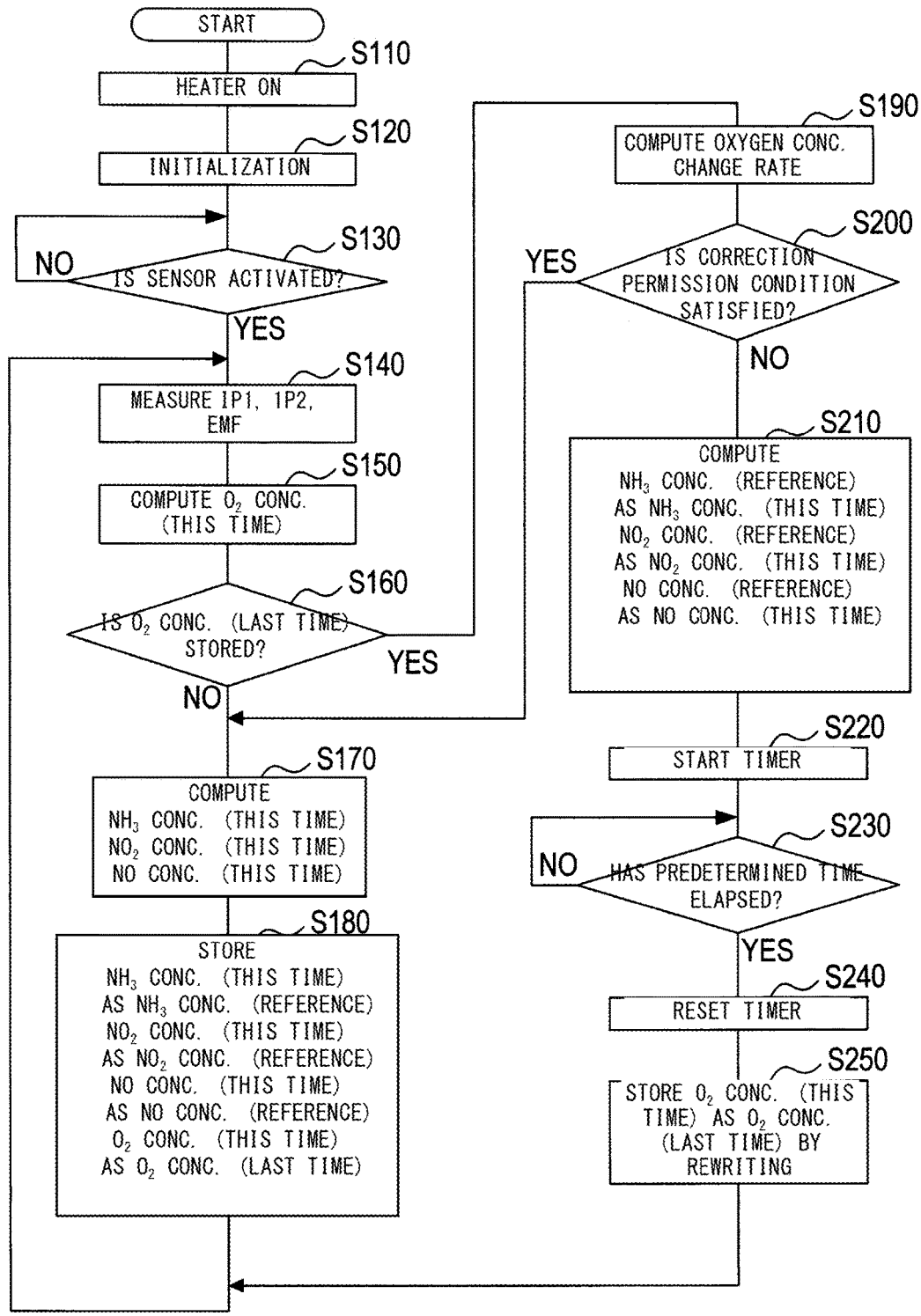
FIG. 6 is a flowchart showing the details of gas concentration computation processing.

FIG. 6 is a flowchart showing the details of the gas concentration computation processing.

When the gas concentration computation processing is started, in S110 (S stands for step), the CPU 61 operates the heater drive circuit 57 so as to cause the heater 19 to generate heat.

In the next S120, the CPU 61 performs initialization, whereby the values of internal variables and the states of internal flags are reset. The internal variables and the internal flags are utilized in the present processing.

In the next S130, the CPU 61 judges whether or not the multi-gas sensor 2 (the first pumping cell 12, the oxygen concentration detection cell 16, the second pumping cell 18, and the ammonia sensor section 21) has been heated to the activation temperature by the heater 19. When the CPU 61 makes an affirmative judgment, the CPU 61 proceeds to S140. When the CPU 61 makes a negative judgment, the CPU 61 waits by repeatedly executing that step (S130).

When the CPU 61 proceeds to S140 as a result of the affirmative judgment in S130, the CPU 61 measures the first pumping current Ip1, the second pumping current Ip2, and the ammonia electromotive force EMF.

In the next S150, the CPU 61 computes the oxygen concentration. Specifically, the computation of the oxygen concentration is executed through use of the first pumping current Ip1 measured in S140 and a relational expression (an expression representing the relation between the first pumping current Ip1 and the oxygen concentration (specifically, the "first pumping current (Ip1)—oxygen concentration relational expression" 63a)) stored in the ROM 63. The CPU 61 stores the obtained oxygen concentration as an "$O_2$ concentration (this time)."

In the next S160, the CPU 61 judges whether or not a value is stored in "$O_2$ concentration (last time)" which is one of the internal variables used for computation by the CPU 61. When the CPU 61 makes an affirmative judgment, the CPU 61 proceeds to S190. When the CPU 61 makes a negative judgment, the CPU 61 proceeds to S170.

Notably, the "$O_2$ concentration (last time)" is an internal variable in which a value is stored in S180 or S250 which will be described later. Namely, in S160, the CPU 61 judges whether or not the processing of storing a value in the "$O_2$ concentration (last time)" in S180 has been executed. Therefore, when S160 is executed first time after the start of the gas concentration computation processing, the CPU 61 makes a negative judgment, and when the number of times of execution of S160 is two or more, the CPU 61 makes an affirmative judgment.

When the CPU 61 proceeds to S170 as a result of the negative judgment in S160, in S170, the CPU 61 computes an "$NH_3$ concentration (this time)", an "$NO_2$ concentration (this time)," and an "NO concentration (this time)."

Specifically, the CPU 61 computes the accurate ammonia concentration (the "corrected ammonia concentration" of claims) which is free from the influence of the concentration of oxygen contained in the gas under measurement through use of the above-described "ammonia concentration output (electromotive force EMF)—ammonia concentration relational expression" 63b, and stores this corrected ammonia concentration as a value of the "$NH_3$ concentration (this time)." The corrected ammonia concentration computed at this time represents the ammonia concentration from which the influence of the oxygen concentration has been removed.

Also, in S170, the CPU 61 computes the $NO_2$ concentration and the NO concentration through use of the above-described "second pumping current (Ip2)—NO concentration relational expression " 63c, "negative ammonia concentration output—$NO_2$ concentration relational expression" 63d, "contributive second pumping current—NO concentration, $NO_2$ concentration relational expression" 63e, "ammonia concentration output—ammonia concentration relational expression" 63f, the second pumping current Ip2 measured in S140, etc. The CPU 61 then stores the computed $NO_2$ concentration and NO concentration as values of the "$NO_2$ concentration (this time)" and the "NO concentration (this time)." Notably, known methods for computing the NO concentration and the $NO_2$ concentration are described in, for example, Japanese Patent Application Laid-Open (kokai) No. 2011-075546. Therefore, the detailed descriptions of the methods are not provided herein.

In the next S180, the CPU 61 executes processing of storing the value of the "NH₃ concentration (this time)" as a value of "NH₃ concentration (reference)," stores the value of the "NO₂ concentration (this time)" as a value of "NO₂ concentration (reference)," stores the value of the "NO concentration (this time)" as a value of "NO concentration (reference)," and stores the value of the "O₂ concentration (this time)" as a value of "O₂ concentration (last time)."

Notably, the "NH₃ concentration (reference)" is an internal variable for storing the latest value among corrected ammonia concentrations computed in the past when a correction permission condition determined on the basis of the oxygen concentration and the oxygen concentration change rate was satisfied. Also, the "NO₂ concentration (reference)" is an internal variable for storing the latest value among NO₂ concentrations computed in the past when the correction permission condition was satisfied. Further, the "NO concentration (reference)" is an internal variable for storing the latest value among NO concentrations computed in the past when the correction permission condition was satisfied.

Meanwhile, when the CPU 61 proceeds to S190 as a result of the affirmative judgment in S160, in S190, the CPU 61 computes an oxygen concentration change rate RA through use of the "O₂ concentration (this time)" and the "O₂ concentration (last time)." Specially, through use of a [Mathematical Expression 1], the CPU 61 divides the "O₂ concentration (last time)" by the "O₂ concentration (this time)" so as to compute the oxygen concentration change rate RA.

MATHEMATICAL EXPRESSION 1

$$RA = \frac{O_2 \text{ concentration (last time)}}{O_2 \text{ concentration (this time)}}$$

In the next S200, the CPU 61 judges whether or not the correction permission condition for the correction of the ammonia concentration by the oxygen concentration is satisfied. When the CPU 61 makes an affirmative judgment, the CPU 61 proceeds to S170. When the CPU 61 makes a negative judgment, the CPU 61 proceeds to S210.

Specifically, in the case where the "O₂ concentration (this time)" exceeds a predetermined reference concentration (in the present embodiment, 4%) and the oxygen concentration change rate is less than a predetermined reference judgment value (in the present embodiment, 1.5), the CPU 61 judges that the correction permission condition is satisfied (affirmative judgment). Notably, in the case where the "O₂ concentration (this time)" is equal to or less than the reference concentration (in the present embodiment, 4%) or the oxygen concentration change rate is equal to or greater than the reference judgment value (in the present embodiment, 1.5), the CPU 61 judges that the correction permission condition is not satisfied (negative judgment).

Notably, the reference concentration for the oxygen concentration used for determining whether or not the correction permission condition is satisfied is set in advance on the basis of, for example, the numerical range of the oxygen concentration within which the detection error of the ammonia concentration falls within an allowable range when the corrected ammonia concentration is computed. Similarly, the reference judgment value for the oxygen concentration change rate used for determining whether or not the correction permission condition is satisfied is set in advance on the basis of, for example, the numerical range of the oxygen concentration change rate within which the detection error of the ammonia concentration falls within the allowable range when the corrected ammonia concentration is computed.

When the CPU 61 proceeds to S210 as a result of the negative judgment in S200, in S210, the CPU 61 performs processing of computing (substituting) the value of the "NH₃ concentration (reference)" as a value of "NH₃ concentration (this time)," computing (substituting) the value of the "NO₂ concentration (reference)" as a value of the "NO₂ concentration (this time)," and computing (substituting) the value of the "NO concentration (reference)" as a value of the "NO concentration (this time)."

In the next S220, the CPU 61 starts timer processing to thereby start timer count.

In the next S230, the CPU 61 judges whether or not a predetermined stop period has elapsed from the point in time (base point) at which the timer count was started in S220. When the CPU 61 makes an affirmative judgment, the CPU 61 proceeds to S240. When the CPU 61 makes a negative judgment, the CPU 61 waits by repeatedly executing that step (S230). Notably, in the present embodiment, 5.0 sec is set as the stop period.

When the CPU 61 proceeds to S240 as a result of the affirmative judgment in S230, in S240, the CPU 61 stops the timer processing to thereby reset the timer count.

In the next S250, the CPU 61 executes processing of storing the value of the "O₂ concentration (this time)" as a value of the "O₂ concentration (last time)."

When the processing of S180 or S250 ends, the CPU 61 again proceeds to S140.

The CPU 61, which executes the gas concentration computation processing in this manner, updates the values of the "NH₃ concentration (this time)," the "NH₃ concentration (reference)," the "NO₂ concentration (this time)," the "NO₂ concentration (reference)," the "NO concentration (this time)," the "NO concentration (reference)," the "O₂ concentration (this time)," and the "O₂ concentration (last time)." Notably, the CPU 61 ends the gas concentration computation processing when the internal combustion engine is stopped.

In concentration output processing separately executed by the CPU 61, the CPU 61 executes processing of outputting to the ECU 200 the value of the "NH₃ concentration (this time)" as an ammonia concentration, the value of the "NO₂ concentration (this time)" as an NO₂ concentration, and the value of the "NO concentration (this time)" as an NO concentration. Notably, the concentration output processing is repeatedly executed at predetermined intervals.

1-7. Measurement Test

Next, there will be described the results of a measurement test in which the ammonia concentration was measured through use of the multi-gas sensor control apparatus 1.

In the present measurement test, a sample gas whose ammonia concentration was controlled to a constant concentration and whose oxygen concentration was varied was used as a gas under measurement. Also, as a comparative example, there was measured the ammonia concentration computed when correction using the correction permission condition was not performed.

Figure 7:
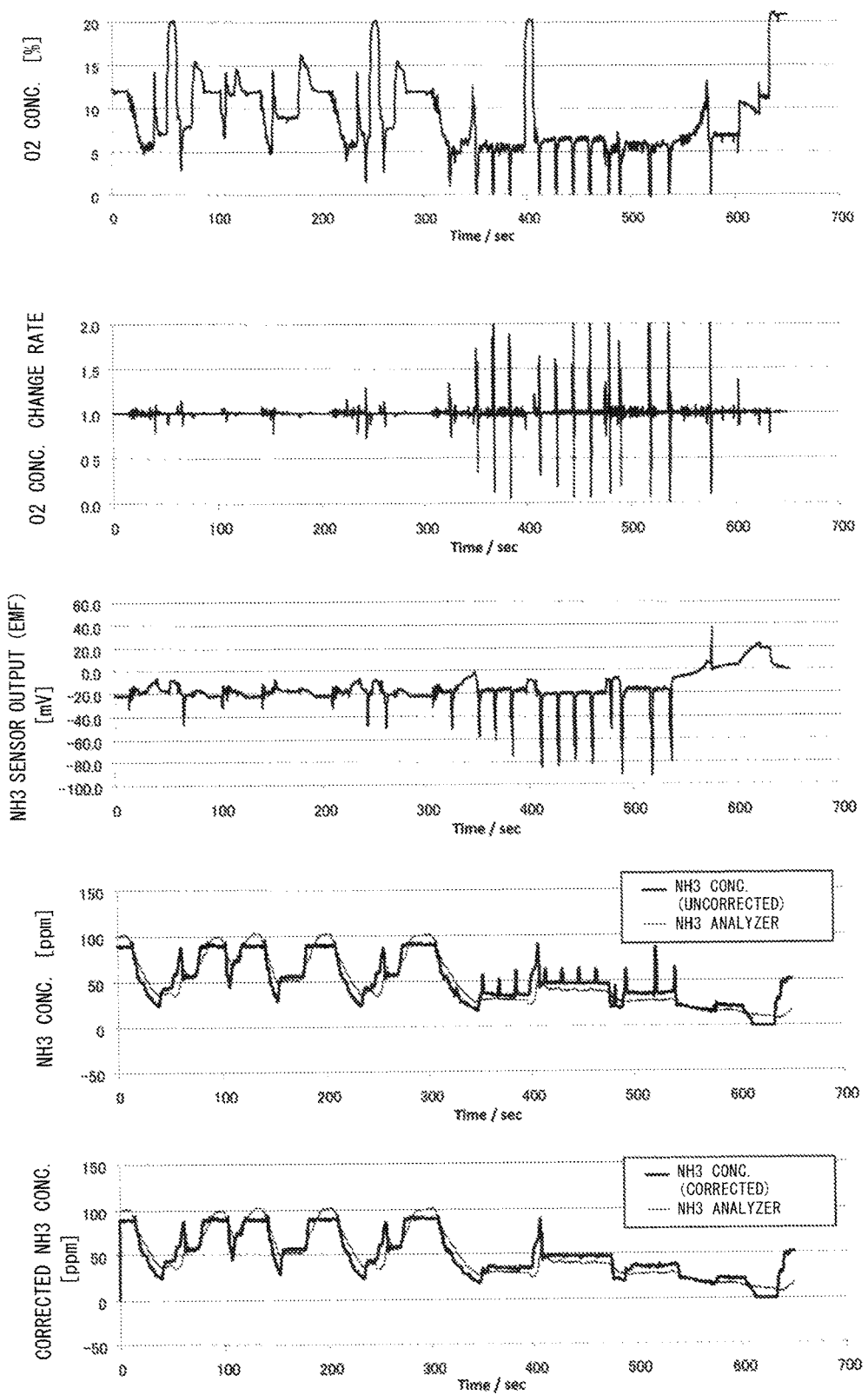
FIG. 7 is an explanatory graphs showing the measurement results of a measurement test in which ammonia concentration was measured through use of the multi-gas sensor control apparatus.

FIG. 7 shows the test results. Notably, FIG. 7 shows five waveforms. Namely, a waveform (O₂ concentration [%]) showing the oxygen concentration of the sample gas, a waveform (O₂ concentration change rate) showing the oxygen concentration change rate, a waveform (NH₃ sensor output EMF [mV]) showing the NH₃ sensor output (ammonia electromotive force EMF), a waveform (NH₃ concentration [ppm]) showing the ammonia concentration (NH₃ concentration (uncorrected)) computed when the correction using the correction permission condition was not performed, and a waveform (corrected $NH_3$ concentration [ppm]) showing the ammonia concentration ($NH_3$ concentration (corrected)) computed through use of the multi-gas sensor control apparatus 1 of the present embodiment are shown in this order from the upper side.

Also, each of the waveforms showing the $NH_3$ concentration (uncorrected) and the $NH_3$ concentration (corrected) is accompanied by an ammonia concentration measured by an ammonia analyzer.

The measurement results show that the ammonia concentration ($NH_3$ concentration (corrected)) of the present embodiment has a waveform closer to the waveform of the ammonia concentration measured by the ammonia analyzer as compared with the ammonia concentration ($NH_3$ concentration (uncorrected)) of the comparative example.

In particular, in a period of 350 sec to 550 sec (lapsed time), the oxygen concentration changed sharply a large number of times, and the oxygen concentration change rate changed greatly a large number of times. Therefore, in the case of the ammonia concentration ($NH_3$ concentration (uncorrected)) of the comparative example, its value changed instantaneously at many locations by receiving the influence of the sharp changes of the oxygen concentration. In contrast, in the case of the ammonia concentration ($NH_3$ concentration (corrected)) of the present embodiment, in the period of 350 sec to 550 sec (lapsed time), its value changed instantaneously at a fewer locations as compared with the ammonia concentration ($NH_3$ concentration (uncorrected)) of the comparative example.

Namely, through use of the multi-gas sensor control apparatus 1 of the present embodiment, it becomes possible to measure the ammonia concentration while suppressing the influence of sharp changes in the oxygen concentration, to thereby suppress a decrease in the accuracy in detecting the ammonia concentration.

1-8. Effects

As described above, the multi-gas sensor control apparatus 1 of the present embodiment is a control apparatus for controlling the multi-gas sensor 2 including the $NO_x$ sensor section 11 and the ammonia sensor section 21. The CPU 61 of the microcomputer 60 executes the gas concentration computation processing to thereby compute the concentrations of ammonia, $NO_2$, and NO contained in the gas under measurement.

As to the ammonia concentration, the CPU 61 computes accurate ammonia concentration (corrected ammonia concentration) which is free from the influence of the concentration of oxygen contained in the gas under measurement through use of the "ammonia concentration output (electromotive force EMF)—ammonia concentration relational expression" 63b.

Also, in the gas concentration computation processing, in accordance with the result of the judgment as to whether or not the correction permission condition is satisfied (S200), the CPU 61 switches its operation between an operation of computing the latest corrected ammonia concentration as the value of the "$NH_3$ concentration (this time)" (S170) and an operation of computing (substituting) the value of the "$NH_3$ concentration (reference)" as the value of the "$NH_3$ concentration (this time)" (S210).

Notably, the correction permission condition regarding the oxygen concentration is set in advance on the basis of, for example, the numerical range of the oxygen concentration within which the detection error of the ammonia concentration falls within the allowable range when the corrected ammonia concentration is computed. Similarly, the correction permission condition regarding the oxygen concentration change rate is set in advance on the basis of, for example, the numerical range of the oxygen concentration change rate within which the detection error of the ammonia concentration falls within the allowable range when the corrected ammonia concentration is computed.

Namely, in the case where the correction permission condition determined on the basis of the oxygen concentration and the oxygen concentration change rate is satisfied, the ammonia concentration detection error in the corrected ammonia concentration falls within the allowable range. Therefore, when the corrected ammonia concentration is set to the "$NH_3$ concentration (this time)" (the detection result of the ammonia concentration), the ammonia concentration detection accuracy does not decrease.

Meanwhile, in the case where at least one of the oxygen concentration and the oxygen concentration change rate does not satisfy the correction permission condition, the ammonia concentration detection error in the corrected ammonia concentration falls outside the allowable range. Therefore, when the corrected ammonia concentration is set to the "$NH_3$ concentration (this time)," the ammonia concentration detection accuracy decreases. Such a decrease in the ammonia concentration detection accuracy can be suppressed by setting, instead of the corrected ammonia concentration, the "$NH_3$ concentration (reference)" (the latest value among the past corrected ammonia concentrations computed when both the oxygen concentration and the oxygen concentration change rate satisfied the correction permission condition) to the "$NH_3$ concentration (this time)."

Namely, in the case where the actual ammonia concentration did not change greatly and the oxygen concentration changed, it is considered that the "$NH_3$ concentration (reference)" has a value close to the actual ammonia concentration. Therefore, a decrease in the ammonia concentration detection accuracy can be suppressed by setting the "$NH_3$ concentration (reference)" to the "$NH_3$ concentration (this time)."

Therefore, in the case where the multi-gas sensor 2 for detecting the concentrations of nitrogen oxides and ammonia contained in the gas under measurement is used, the present multi-gas sensor control apparatus 1 can suppress a decrease in the accuracy in detecting the ammonia concentration.

Next, in the multi-gas sensor control apparatus 1, in the case where the CPU 61 determines in S200 of the gas concentration computation processing that the oxygen concentration (the "$O_2$ concentration (this time)") exceeds the reference concentration and the oxygen concentration change rate is less than the reference judgment value (in the present embodiment, 1.5), the CPU 61 judges that the correction permission condition is satisfied (affirmative judgment in S200). Meanwhile, in the case where the CPU 61 determines in S200 of the gas concentration computation processing that the oxygen concentration change rate is equal to or greater than the reference judgment value or the oxygen concentration is equal or less than the predetermined reference concentration, the CPU 61 judges that the correction permission condition is not satisfied (negative judgment in S200).

Namely, the oxygen concentration change rate increases as the degree of steepness of the change in the oxygen concentration increases. Therefore, in the case where the oxygen concentration change rate is equal to or greater than the reference judgment value, it is possible to determine that the oxygen concentration changed sharply and judge that the correction permission condition is not satisfied. Notably, as the reference judgment value for the oxygen concentration change rate, there is previously set, for example, a boundary value between an oxygen concentration change rate which causes the ammonia concentration detection error to fall within the allowable range (±5%, preferably, ±3%) when the corrected ammonia concentration is computed and an oxygen concentration change rate which causes the ammonia concentration detection error to deviate from the allowable range when the corrected ammonia concentration is computed.

Also, when the oxygen concentration becomes extremely low, the error of the corrected ammonia concentration tends to increase. Therefore, in the case where the oxygen concentration is equal to or less than the reference concentration, it is possible to determine that the error of the corrected ammonia concentration is large and judge that the correction permission condition is not satisfied. Notably, as the reference concentration for the oxygen concentration, there is previously set, for example, a boundary value between an oxygen concentration which causes the ammonia concentration detection error to fall within the allowable range when the corrected ammonia concentration is computed and an oxygen concentration which causes the ammonia concentration detection error to deviate from the allowable range when the corrected ammonia concentration is computed.

Namely, in this multi-gas sensor control apparatus 1, in the case where the oxygen concentration change rate is equal to or greater than the reference judgment value or the oxygen concentration is equal to or less than the reference concentration, the CPU 61 judges that the correction permission condition is not satisfied and sets the "$NH_3$ concentration (reference)" to the "$NH_3$ concentration (this time)."

Therefore, according to the multi-gas sensor control apparatus 1, a decrease in the ammonia concentration detection accuracy can be suppressed by judging that the correction permission condition is not satisfied when the oxygen concentration change rate is equal to or greater than the reference judgment value or the oxygen concentration is equal to or less than the reference concentration.

Next, in the multi-gas sensor control apparatus 1, until the predetermined stop period elapses after the CPU 61 has judged in S200 of the gas concentration computation processing that the correction permission condition is not satisfied (negative judgment in S200), the CPU 61 determines that the correction permission condition is not satisfied. Specifically, until the stop period elapses after the CPU 61 has made the negative judgment in S200, the CPU 61 stops the updating of the "$NH_3$ concentration (this time)" to thereby maintains the state in which the "$NH_3$ concentration (reference)" has been set to the "$NH_3$ concentration (this time)."

Namely, when it is judged that at least one of the oxygen concentration and the oxygen concentration change rate does not satisfy the correction permission condition, there is a high possibility that, during a certain period after that, the influence of the oxygen concentration remains and the corrected ammonia concentration has an error.

In view of this, until the stop period elapses after the judgment that at least one of the oxygen concentration and the oxygen concentration change rate does not satisfy the correction permission condition, the CPU 61 judges that the correction permission condition is not satisfied and maintains the state in which the "$NH_3$ concentration (reference)" has been set to the "$NH_3$ concentration (this time)."

As a result, it is possible to avoid a corrected ammonia concentration which is highly likely to involve an error from being set to the "$NH_3$ concentration (this time)." Therefore, according to this multi-gas sensor control apparatus 1, a decrease in the ammonia concentration detection accuracy can be suppressed further.

Next, in the multi-gas sensor control apparatus 1, the CPU 61 computes the oxygen concentration change rate in S190 of the gas concentration computation processing by dividing the oxygen concentration computed last time by the oxygen concentration computed this time.

Namely, in computation of the oxygen concentration change rate, a value obtained by dividing the "$O_2$ concentration (last time)" (the oxygen concentration computed last time) by the "$O_2$ concentration (this time)" (the oxygen concentration computed this time) is computed as the oxygen concentration change rate. As a result, when the oxygen concentration decreases, the oxygen concentration change rate assumes a large value. Therefore, the oxygen concentration change rate changes greatly as a result of a small change in the oxygen concentration, whereby the judgment as to whether or not the oxygen concentration change rate has changed can be made easily.

Therefore, according to the multi-gas sensor control apparatus 1, it is possible to improve the accuracy of the judgment based on the oxygen concentration change rate, to thereby suppress a decrease in the ammonia concentration detection accuracy to a greater degree.

1-9. Correspondence Between Embodiment and Claims

A description will be given of the correspondence between terms used in claims and terms used in the present embodiment.

The first pumping cell 12 corresponds to an example of the first pumping cell; the second pumping cell 18 corresponds to an example of the second pumping cell; the $NO_x$ sensor section 11 corresponds to an example of the $NO_x$ sensor section; the ammonia sensor section 21 corresponds to an example of the ammonia sensor section; the multi-gas sensor 2 corresponds to an example of the multi-gas sensor; and the multi-gas sensor control apparatus 1 corresponds to an example of the sensor control apparatus.

S150 of the gas concentration computation processing corresponds to an example of the oxygen concentration computation step; S170 of the gas concentration computation processing corresponds to an example of the corrected concentration computation step; S190 of the gas concentration computation processing corresponds to an example of the oxygen concentration change rate computation step; and S200, S80, S210, S220, S230, and S240 of the gas concentration computation processing correspond to an example of the ammonia concentration setting step.

The microcomputer 60 which executes S150 of the gas concentration computation processing corresponds to an example of the oxygen concentration computation section; the microcomputer 60 which executes S170 of the gas concentration computation processing corresponds to an example of the corrected concentration computation section; and the microcomputer 60 which executes S190 of the gas concentration computation processing corresponds to an example of the oxygen concentration change rate computation section. The microcomputer 60 which executes S200, S180, S210, S220, S230, and S240 of the gas concentration computation processing corresponds to an example of the ammonia concentration setting section.

2. Modified Embodiment 1

Next, a modified embodiment 1 of the present invention will be described. Notably, a multi-gas sensor control apparatus 201 of the modified embodiment 1 differs from the multi-gas sensor control apparatus 1 of the first embodiment in the structure of the sensor element section 10 (in particular, the structure of the ammonia sensor section 21), the control section 3, and the data stored in the ROM 63 of the microcomputer 60. The differences in the control section 3 and the data are attributable to the difference in the structure of the ammonia sensor section 21.

In the following description of the multi-gas sensor control apparatus 201 of the modified embodiment 1, points differing from the multi-gas sensor control apparatus 1 of the first embodiment will be described, and the same points as the multi-gas sensor control apparatus 1 of the first embodiment will be described through use of the same reference numerals as those used for the first embodiment or their descriptions will be omitted.

2-1. Sensor Element Section

Figure 8:
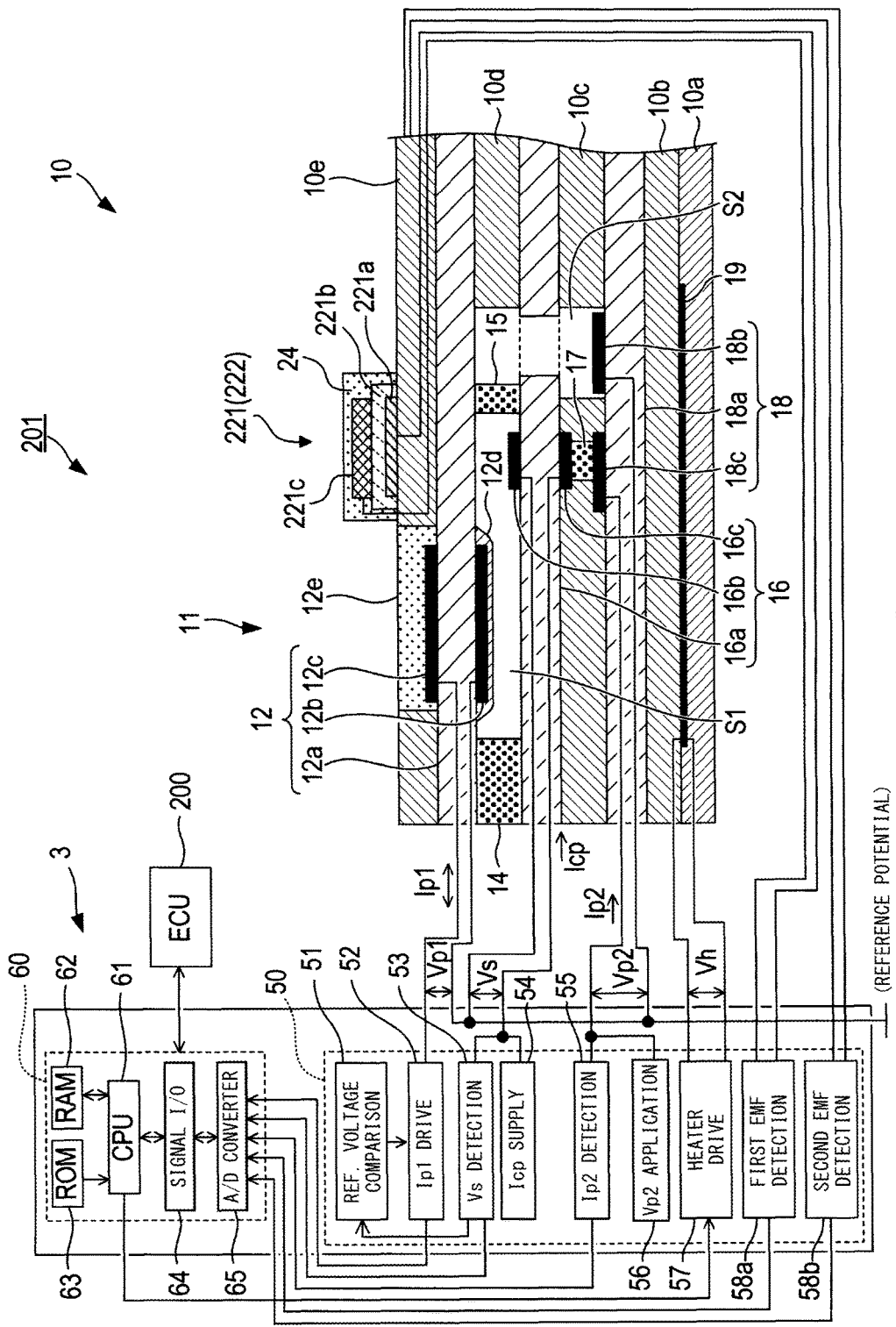
FIG. 8 is a block diagram describing the configuration of a multi-gas sensor control apparatus of a modified embodiment 1.

FIG. 8 only shows a schematic sectional view of the sensor element section 10 of the multi-gas sensor control apparatus 201 of the modified embodiment 1 along the longitudinal direction thereof.

An $NO_x$ sensor section 11, a first ammonia sensor section 221, and a second ammonia sensor section 222 are mainly provided in the sensor element section 10. Since the $NO_x$ sensor section 11 of the modified embodiment 1 has the same structure as the first embodiment, its description is not repeated.

The first ammonia sensor section 221 and the second ammonia sensor section 222 are disposed at approximately the same position as the reference electrode 16c in the longitudinal direction of the $NO_x$ sensor section 11 (the left-right direction of FIG. 8) such that their positions in the width direction of the NOx sensor section 11 (the front-back direction of FIG. 8) differ from each other.

Figure 9:
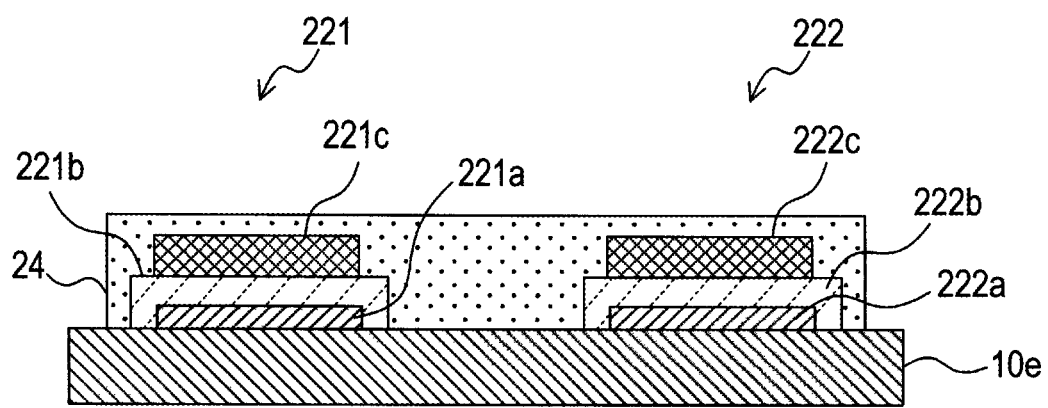
FIG. 9 is a sectional view showing the structures of a first ammonia sensor section and a second ammonia sensor section in a sensor element section.

FIG. 9 is a sectional view showing the structures of the first ammonia sensor section 221 and the second ammonia sensor section 222. Notably, the left-right direction in FIG. 9 corresponds to the width direction of the $NO_x$ sensor section 11.

As shown in FIGS. 8 and 9, the first ammonia sensor section 221 and the second ammonia sensor section 222 are formed on the outer surface of the $NO_x$ sensor section 11; more specifically, on the insulating layer 10e. The first ammonia sensor section 221 is configured such that a first reference electrode 221a is formed on the insulating layer 10e, and a first solid electrolyte member 221b covers the upper and side surfaces of the first reference electrode 221a. Further, a first detection electrode 221c is formed on the surface of the first solid electrolyte member 221b. The concentration of ammonia contained in the gas under measurement is detected on the basis of a change in the electromotive force between the first reference electrode 221a and the first detection electrode 221c.

Similarly, the second ammonia sensor section 222 is configured such that a second reference electrode 222a is formed on the insulating layer 10e, and a second solid electrolyte member 222b covers the upper and side surfaces of the second reference electrode 222a. Further, a second detection electrode 222c is formed on the surface of the second solid electrolyte member 222b.

The first detection electrode 221c and the second detection electrode 222c may be formed of a material which contains Au as a main component (for example, 70 mass % or more). The first reference electrode 221a and the second reference electrode 222a may be formed of Pt only or a material which contains Pt as a main component (for example, 70 mass % or more). The first solid electrolyte member 221b and the second solid electrolyte member 222b are formed of, for example, partially stabilized zirconia (YSZ).

Also, a diffusion layer 24 (protection layer 24) made of a porous material is formed to completely cover the first detection electrode 221c, the first solid electrolyte member 221b, the second detection electrode 222c, and the second solid electrolyte member 222b. The diffusion layer 24 can adjust the diffusion speed of the gas under measurement which flows into the first ammonia sensor section 221 and the second ammonia sensor section 222 from the outside.

As in the first embodiment, the diffusion layer 24 is formed of at least one material selected from the group consisting of alumina, spinel ($MgAl_2O_4$), silica alumina, and mullite.

2-2. Control Section

A control circuit 50 of the control section 3 of the multi-gas sensor control apparatus 201 is mainly composed of a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, a first electromotive force detection circuit 58a, and a second electromotive force detection circuit 58b. Since the reference voltage comparison circuit 51, the Ip1 drive circuit 52, the Vs detection circuit 53, the Icp supply circuit 54, the Ip2 detection circuit 55, the Vp2 application circuit 56, and the heater drive circuit 57 of the control circuit 50 of the modified embodiment have the same configurations as those of the first embodiment, their descriptions will not be repeated.

The first electromotive force detection circuit 58a is electrically connected to the first detection electrode 221c and the first reference electrode 221a of the first ammonia sensor section 221. The second electromotive force detection circuit 58b is electrically connected to the second detection electrode 222c and the second reference electrode 222a of the second ammonia sensor section 222. The first electromotive force detection circuit 58a detects a first ammonia electromotive force EMF which is the electromotive force between the first detection electrode 221c and the first reference electrode 221a and outputs the detected first ammonia electromotive force EMF to the microcomputer 60. Similarly, the second electromotive force detection circuit 58b detects a second ammonia electromotive force EMF which is the electromotive force between the second detection electrode 222c and the second reference electrode 222a and outputs the detected second ammonia electromotive force EMF to the microcomputer 60.

2-3. Microcomputer

Various types of data (relational expressions) which will be described below are stored in the ROM 63 of the microcomputer 60. The CPU 61 reads the various types of data from in the ROM 63 and performs various types of computation processing by using the value of the first pumping current Ip1, the value of the second pumping current Ip2, the first ammonia electromotive force, and the second ammonia electromotive force.

The ROM 63 stores a "first ammonia concentration output (electromotive force EMF)—first ammonia concentration relational expression," a "second ammonia concentration output (electromotive force EMF)—second ammonia concentration relational expression," a "first pumping current (Ip1)—oxygen concentration relational expression," a "second pumping current (Ip2)—$NO_x$ concentration relational expression," a "first ammonia concentration & second ammonia concentration & oxygen concentration—corrected ammonia concentration relational expression" (correction expression (1): see the following), a "first ammonia concentration & second ammonia concentration & oxygen concentration output—corrected $NO_2$ concentration relational expression" (correction expression (2)), and an "$NO_x$ concentration & corrected ammonia concentration & corrected $NO_2$ concentration—corrected NO concentration relational expression" (correction expression (3)).

The various types of data may be set as predetermined relational expressions as described above. However, the various types of data may be, for example, tables which allow calculation of various types of gas concentrations from the output of the sensor. Also, the various types of data may be values (relational expressions, tables, etc.) obtained through use of, for example, model gases whose gas concentrations are known.

The "first ammonia concentration output—first ammonia concentration relational expression" and the "second ammonia concentration output—second ammonia concentration relational expression" are expressions which represent the relations between the ammonia concentration outputs output from the first ammonia sensor section 221 and the second ammonia sensor section 222 and the concentration of ammonia contained in the gas under measurement, The "first pumping current—oxygen concentration relational expression" is an expression which represents the relation between the first pumping current and the concentration of oxygen contained in the gas under measurement. The "second pumping current—$NO_x$ concentration relational expression" is an expression which represents the relation between the second pumping current and the concentration of $NO_x$ contained in the gas under measurement.

The "first ammonia concentration & second ammonia concentration & oxygen concentration—corrected ammonia concentration relational expression" is an expression which represents the relation between the (first and second) ammonia concentrations influenced by the oxygen concentration and the $NO_2$ concentration and the corrected ammonia concentration output from which the influences of the oxygen concentration and the $NO_2$ concentration have been removed. The "first ammonia concentration & second ammonia concentration & oxygen concentration output—corrected $NO_2$ concentration relational expression" is an expression which represents the relation between the $NO_2$ concentration influenced by the oxygen concentration and the ammonia concentration and the corrected $NO_2$ concentration output from which the influences of the oxygen concentration and the ammonia concentration have been removed. The "$NO_x$ concentration & corrected ammonia concentration & corrected $NO_2$ concentration—corrected NO concentration relational expression" is an expression which represents the relation between the $NO_x$ concentration influenced by the ammonia concentration and the $NO_2$ concentration and the accurate corrected NO concentration from which the influences of the ammonia concentration and the $NO_2$ concentration have been removed through correction.

Next, there will be described the computation processing which is executed by the CPU 61 of the microcomputer 60 so as to obtain the corrected NO concentration, the corrected $NO_2$ concentration, and the corrected ammonia concentration from the first pumping current Ip1, the second pumping current Ip2, the first ammonia concentration output, and the second ammonia concentration output.

When the first pumping current Ip1, the second pumping current Ip2, the first ammonia concentration output, and the second ammonia concentration output are input, the CPU 61 performs the computation processing for obtaining the oxygen concentration, the $NO_x$ concentration, the first ammonia concentration, and the second ammonia concentration. Specially, the CPU 61 invokes the "first ammonia concentration output—first ammonia concentration relational expression," the "second ammonia concentration output —second ammonia concentration relational expression," the "first pumping current Ip1—oxygen concentration relational expression," and the "second pumping current Ip2—$NO_x$ concentration relational expression" from the ROM 63, and performs processing of calculating respective concentration outputs through use of the relational expressions. After having obtained the oxygen concentration, the $NO_x$ concentration, the first ammonia concentration, and the second ammonia concentration, the CPU 61 obtains the corrected ammonia concentration, the corrected NO concentration, and the corrected $NO_2$ concentration by performing computation through use of correction expressions which will be described below.

Correction expression (1)
$$x = F(A, B, D) \\ = (eA - c)*(jB - h - fA + d)/(eA - c - iB + g) + fA - d$$

Correction expression (2)
$$y = F'(A, B, D) \\ = (jB - h - fA + d)/(eA - c - iB + g)$$

Correction expression (3)
$$z = C - ax + by$$

In these expressions, x is the corrected ammonia concentration, y is the corrected $NO_2$ concentration, and z is the NO concentration. Also, A is the first ammonia concentration, B is the second ammonia concentration, C is the $NO_x$ concentration, and D is the oxygen concentration. F and F' of the correction expressions (1) and (2) show that x is a function of (A, B, D). Further, a and b are correction coefficients, and c, d, e, f, g, h, i, and j are coefficients calculated through use of the oxygen concentration D (coefficients determined by D).

The CPU 61 obtains the corrected ammonia concentration, corrected $NO_2$ concentration, and corrected NO concentration of the gas under measurement by substituting the first ammonia concentration, the second ammonia concentration, the $NO_x$ concentration, and the oxygen concentration into the above-described correction expressions (1) to (3).

Notably, the correction expressions (1) and (2) are expressions determined on the basis of the characteristics of the first ammonia sensor section 221 and the second ammonia sensor section 222, and the correction expression (3) is an expression determined on the basis of the characteristics of the $NO_x$ sensor section 11. The correction expressions (1) to (3) show examples of correction expressions, and other correction expressions, coefficients, etc. may be properly changed in accordance with the gas detection characteristics.

2-4. Effect

In the case where a multi-gas sensor for detecting the concentrations of nitrogen oxides and ammonia contained in the gas under measurement is used, like the multi-gas sensor control apparatus 1, the multi-gas sensor control apparatus 201 of the modified embodiment 1 can suppress a decrease in the accuracy in detecting the ammonia concentration.

3. Modified Embodiment 2

Next, a modified embodiment 2 of the present invention will be described. Notably, a multi-gas sensor control apparatus of the modified embodiment 2 differs from the multi-gas sensor control apparatus 1 of the first embodiment in the gas concentration computation processing. In the following description of the multi-gas sensor control apparatus of the modified embodiment 2, points differing from the multi-gas sensor control apparatus 1 of the first embodiment will be described, and the same points as the multi-gas sensor control apparatus 1 of the first embodiment will be described through use of the same reference numerals as those used for the first embodiment or their descriptions will be omitted.

Figure 10:
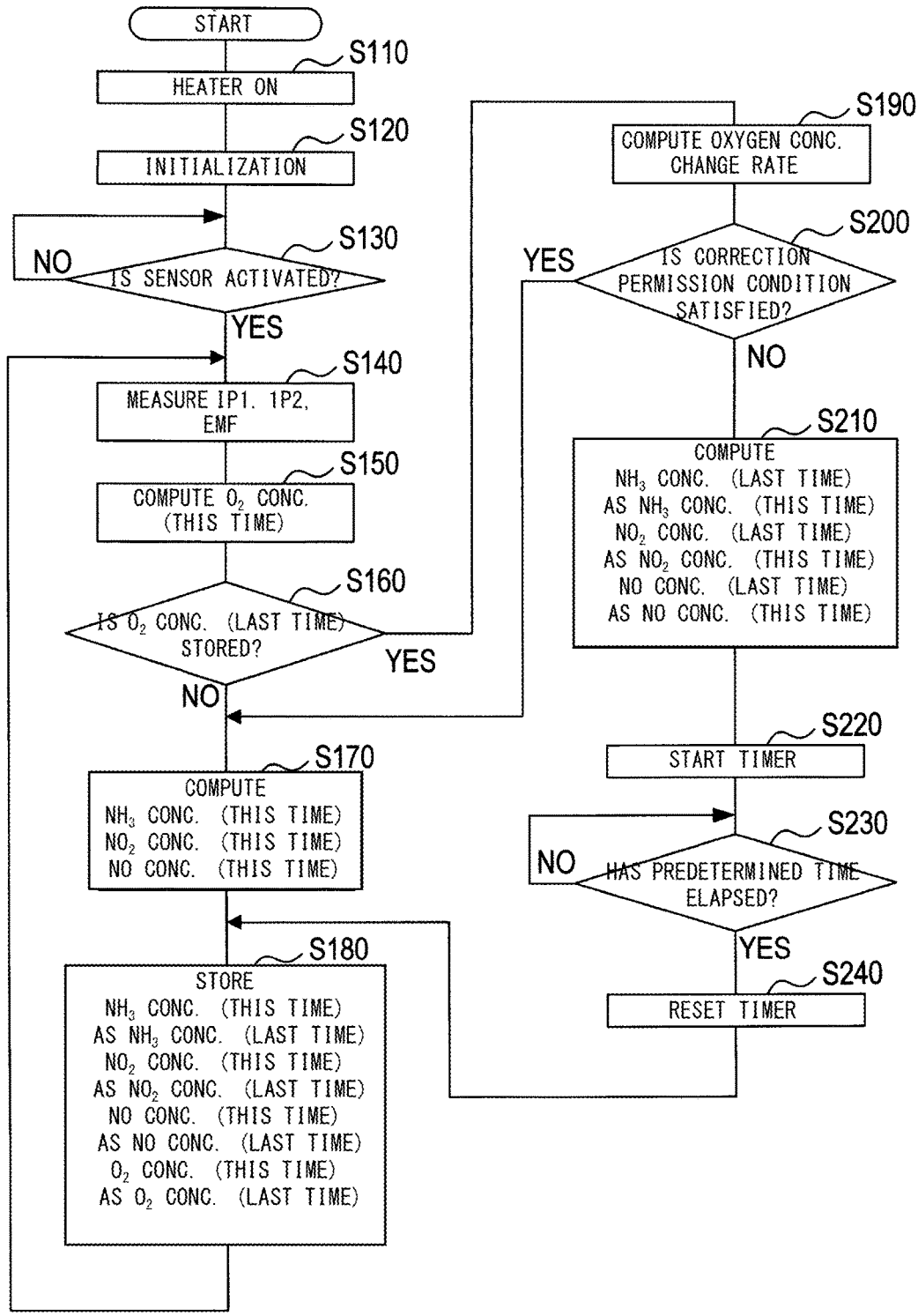
FIG. 10 is a flowchart showing the details of gas concentration computation processing in a modified embodiment 2.

FIG. 10 is a flowchart showing the details of the gas concentration computation processing. Notably, since S110 to S170, S190 to S200, and S220 to S240 are the same as the first embodiment, their descriptions will not be repeated.

In the gas concentration computation processing of the modified embodiment 2, in S180, the CPU 61 executes processing of storing the value of the "$NH_3$ concentration (this time)" as a value of "$NH_3$ concentration (last time)," stores the value of the "$NO_2$ concentration (this time)" as a value of "$NO_2$ concentration (last time)," stores the value of the "NO concentration (this time)" as a value of "NO concentration (last time)," and stores the value of the "$O_2$ concentration (this time)" as a value of "$O_2$ concentration (last time)."

Also, in the gas concentration computation processing of the modified embodiment 2, when the CPU 61 proceeds to S210 as a result of the negative judgment in S200, in S210, the CPU 61 performs processing of computing (substituting) the value of the "$NH_3$ concentration (last time)" as a value of "$NH_3$ concentration (this time)," computing (substituting) the value of the "$NO_2$ concentration (last time)" as a value of the "$NO_2$ concentration (this time)," and computing (substituting) the value of the "NO concentration (last time)" as a value of the "NO concentration (this time)."

Also, in the gas concentration computation processing of the modified embodiment 2, the CPU 61 stops the timer processing in S240 to thereby reset the timer count, and then proceeds to S180.

In the multi-gas sensor control apparatus of the modified embodiment 2 configured as described above, when the correction permission condition is satisfied (affirmative judgment in S200), the corrected ammonia concentration of this time is set to the detection result of the ammonia concentration of this time ($NH_3$ concentration (this time)) (S170). Also, in the multi-gas sensor control apparatus, when the correction permission condition is not satisfied (negative judgment in S200), the ammonia concentration set to the detection result of the last time ($NH_3$ concentration (last time)) is set to the detection result of the ammonia concentration of this time ($NH_3$ concentration (this time)) (S210).

Namely, since the numerical value set to the detection result of the ammonia concentration ($NH_3$ concentration (this time)) is the corrected ammonia concentration computed when the correction permission condition was satisfied, the ammonia concentration set to the detection result of the last time ($NH_3$ concentration (last time)) is also the corrected ammonia concentration computed when the correction permission condition was satisfied. Since the ammonia concentration set to the detection result of the last time ($NH_3$ concentration (last time)) is the latest corrected ammonia concentration among the past corrected ammonia concentrations computed when the correction permission condition was satisfied, the ammonia concentration set to the detection result of the last time ($NH_3$ concentration (last time)) assumes a value close to the actual ammonia concentration.

Therefore, a decrease in the ammonia concentration detection accuracy can be suppressed as a result of the ammonia concentration set to the detection result of the last time ($NH_3$ concentration (last time)) being set to the detection result of the ammonia concentration of this time ($NH_3$ concentration (this time)).

Accordingly, in the case where a multi-gas sensor for detecting the concentrations of nitrogen oxides and ammonia contained in the gas under measurement is used, like the multi-gas sensor control apparatus 1, the multi-gas sensor control apparatus of the modified embodiment 2 can suppress a decrease in the accuracy in detecting the ammonia concentration.

4. Modified Embodiment 3

Next, a modified embodiment 3 of the present invention will be described. Notably, a sensor control apparatus 301 of the modified embodiment 3 differs from the multi-gas sensor control apparatus 1 of the first embodiment in that separate-type sensor 540 is provided in place of the multi-gas sensor 2. The separate-type sensor 540 includes an $NO_x$ sensor 541 and an ammonia sensor 542 formed separately, and the $NO_x$ sensor 541 and the ammonia sensor 542 can be disposed individually such that they are separated from each other.

In the following description of the multi-gas sensor control apparatus 301 of the modified embodiment 3, points differing from the multi-gas sensor control apparatus 1 of the first embodiment will be described, and the same points as the multi-gas sensor control apparatus 1 of the first embodiment will be described through use of the same reference numerals as those used for the first embodiment or their descriptions will be omitted.

4-1. Sensor Control Apparatus

Figure 11:
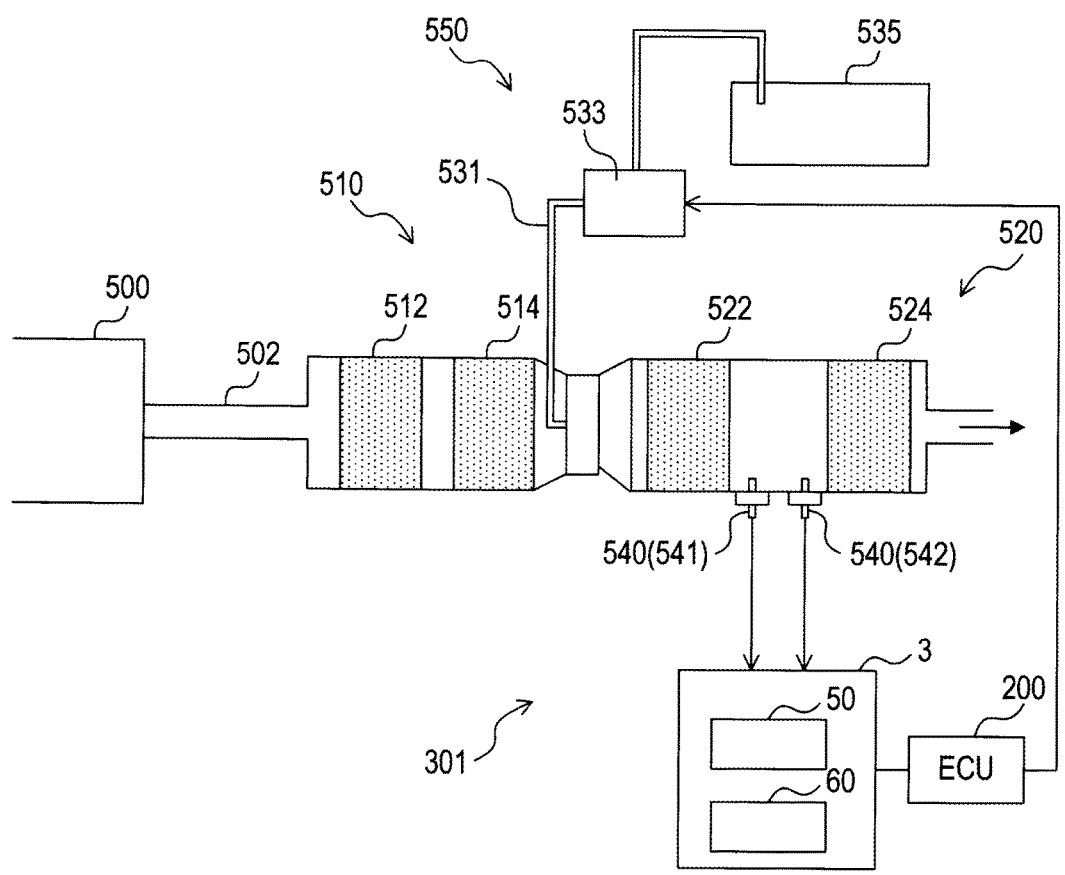
FIG. 11 is a block diagram describing the configuration of a sensor control apparatus of a modified embodiment 3.

FIG. 11 is a block diagram describing the configuration of the sensor control apparatus 301 of the modified embodiment 3.

The sensor control apparatus 301 includes the separate-type sensor 540 (the $NO_x$ sensor 541 and the ammonia sensor 542) and a control section 3 (computation section 3) which controls the sensor and processes the sensor outputs to thereby compute the concentrations of NO, $NO_2$, and ammonia.

The separate-type sensor 540 (the $NO_x$ sensor 541 and the ammonia sensor 542) is provided on an exhaust pipe 502 (exhaust path 502) of an engine 500 (diesel engine 500) which is an internal combustion engine of a vehicle.

Since the control section 3 is the same as the control section 3 of the first embodiment, its description will not be repeated.

4-2. Exhaust Purification Apparatus

An exhaust purification apparatus 550 for purifying exhaust gas discharged from the engine 500 is attached to an intermediate portion of the exhaust pipe 502 of the engine 500. The exhaust purification apparatus 550 includes an upstream side exhaust purification apparatus 510 (also referred to as the "DPF apparatus 510"), a downstream side exhaust purification apparatus 520 (also referred to as the "SCR apparatus 520," and a urea water addition nozzle 531. The upstream side exhaust purification apparatus 510 is disposed in the exhaust pipe 502 to be located on the upstream side of the downstream side exhaust purification apparatus 520. The urea water addition nozzle 531 is provided between the upstream side exhaust purification apparatus 510 and the downstream side exhaust purification apparatus 520.

The DPF apparatus 510 is constituted by disposing an oxidation catalyst 512 (Diesel Oxidation Catalyst, hereinafter referred to as the "DOC 512") and a particulate filter 514 (Diesel Particulate Filter, hereinafter referred to as the "DPF 514") in a tubular casing of the exhaust pipe 502 in this order from the upstream side. The DPF 514 includes, for example, a porous filter (e.g., ceramic filter) for collecting particulate matter (PM). The DOC 512 includes a honeycomb-shaped substrate which is made of metal, ceramic or the like and which supports a catalytic substance which oxidizes NO to produce $NO_2$. The DOC 512 oxidizes NO contained in the exhaust gas to thereby produce $NO_2$, and the PM collected by the DPF 514 is oxidized through use of this $NO_2$ for combustion removal, whereby the DPF 514 can be regenerated continuously. Notably, the regeneration control for the DPF 514 is performed by the ECU 200.

The SCR apparatus 520 is constituted by disposing a selective-reduction-type catalyst 522 (Selective Catalytic Reduction, hereinafter referred to as the "SCR 522") and a subsequent stage oxidation catalyst 524 (Clean Up Catalyst, hereinafter referred to as the "CUC 524") in a tubular casing of the exhaust pipe 502 in this order from the upstream side. The SCR apparatus 520 is a catalyst which reduces $NO_x$ contained in the exhaust gas to $N_2$ by using the ammonia supplied from the upstream side as a reducing agent. For example, a zeolite-based catalyst, a vanadium-based catalyst, or the like can be used. The CUC 524 is an oxidation catalyst which removes the ammonia which did not react in the SCR 522.

The urea water addition nozzle 531, to which urea water within a urea water tank 535 is supplied by an addition apparatus 533, injects the urea water into the exhaust gas on the upstream side of the SCR 522. The urea water injected into the exhaust gas on the upstream side of the SCR 522 is hydrolyzed and becomes ammonia, which acts as a reducing agent in the SCR 522. The control of addition of the urea water is controlled by the ECU 200.

The ECU 200 receives from the control section 3 the concentrations of NO, $NO_2$, and ammonia contained in the exhaust gas having passed through the SCR 522, and performs various types of controls for the engine, deterioration judgment for the DOC 512, regeneration control for the DPF 514, urea water addition control, etc. Notably, the ECU 200 includes an electronic control unit (ECU) which is composed of a predetermined analog circuit and a microcomputer including a CPU (central control unit), a RAM, a ROM, etc. The CPU executes a computer program stored in the ROM, whereby various types of processing are performed.

The exhaust path 502 includes a plurality of spaces separated from one another by the DOC 512, the DPF 514, the SCR 522, and the CUC 524. The DOC 512, the DPF 514, the SCR 522, and the CUC 524 are configured such that the exhaust gas can pass through them.

4-3. $NO_x$ Sensor and Ammonia Sensor

The $NO_x$ sensor 541 and the ammonia sensor 542 are disposed in the space between the SCR 522 and the CUC 524 among the plurality of spaces of the exhaust path 502. The $NO_x$ sensor 541 is disposed on the upstream side of the ammonia sensor 542 as viewed in the flow direction of the exhaust gas.

Since the separate-type sensor 540 is configured such that the $NO_x$ sensor 541 and the ammonia sensor 542 are disposed in the same space of the exhaust path 502, it is possible to detect the concentrations of nitrogen oxides (NO and $NO_2$) and ammonia contained in the gas under measurement in the same space.

Although not shown, the $NO_x$ sensor 541 is mainly composed of a sensor element section, a metallic shell, a separator, and connection terminals. The sensor element section of the $NO_x$ sensor 541 is formed as a plate-shaped sensor element section having a sensor section equivalent to the $NO_x$ sensor section 11 in the first embodiment. The $NO_x$ sensor 541 can be configured by using a known $NO_x$ sensor, and a known $NO_x$ sensor is described in, for example, Japanese Patent Application Laid-Open (kokai) No. 2011-164086. Therefore, the detailed description of the $NO_x$ sensor is omitted.

Although not shown, the ammonia sensor 542 is mainly composed of a sensor element section, a metallic shell, a separator, and connection terminals. The sensor element section of the ammonia sensor 542 is formed as a plate-shaped sensor element section having a sensor section equivalent to the ammonia sensor section 21 in the first embodiment. For example, the ammonia sensor section can be formed through use of the constituent elements shown in FIG. 3. The ammonia sensor 542 can be configured by using a known ammonia sensor, and a known ammonia sensor is described in, for example, Japanese Patent Application Laid-Open (kokai) No. 2013-068607, the detailed description of the ammonia sensor is omitted.

Like the $NO_x$ sensor section 11 and the ammonia sensor section 21 of the first embodiment, the sensor element section of the $NO_x$ sensor 541 and the sensor element section of the ammonia sensor 542 are connected to the control section 3.

Like the control section 3 of the first embodiment, the control section 3 of the sensor control apparatus 301 includes a control circuit 50 and a microcomputer 60. The control section 3 controls the $NO_x$ sensor 541 and the ammonia sensor 542 and processes the outputs of the sensors to thereby compute the concentrations of NO, $NO_2$, and ammonia.

4-4. Effects

As described above, the sensor control apparatus 301 differs from the multi-gas sensor control apparatus 1 of the first embodiment in that the separate-type sensor 540 is provided in place of the multi-gas sensor 2. However, the sensor control apparatus 301 is the same as the multi-gas sensor control apparatus 1 in that it computes the concentrations of ammonia, $NO_2$, and NO contained in the gas under measurement by executing the gas concentration computation processing.

The $NO_x$ sensor 541 and the ammonia sensor 542 of the separate-type sensor 540 are disposed in the same space among the plurality of spaces of the exhaust path 502, and the $NO_x$ sensor 541 is disposed on the upstream side of the ammonia sensor 542 in the flow direction of the exhaust gas. Such a separate-type sensor 540 can detect the concentrations of nitrogen oxides and ammonia contained in the gas under measurement (exhaust gas) in the same space, because the $NO_x$ sensor 541 and the ammonia sensor 542 are disposed in the same space among the plurality of spaces of the exhaust path 502.

Therefore, through use of the separate-type sensor 540 having the $NO_x$ sensor 541 and the ammonia sensor 542, the sensor control apparatus 301 can suppress a decrease in the ammonia concentration detection accuracy, like the multi-gas sensor control apparatus 1 of the first embodiment, when the concentrations of nitrogen oxides and ammonia contained in the gas under measurement in the same space are detected.

Also, the $NO_x$ sensor 541 is disposed on the upstream side of the ammonia sensor 542 in the flow direction of the exhaust gas. Since the relative positional relationship between the $NO_x$ sensor 541 and the ammonia sensor 542 is determined in this manner, the oxygen concentration detection position is located on the upstream side of the ammonia concentration detection position in the flow direction of the exhaust gas. In this case, in computation of the corrected ammonia concentration, the oxygen concentration detected on the upstream side of the ammonia concentration detection position can be used. As a result, the detection timing of the oxygen concentration does not fall behind the detection timing of the ammonia concentration, and the corrected ammonia concentration can be computed accurately.

Therefore, according to the sensor control apparatus 301, the corrected ammonia concentration can be computed accurately, whereby a decrease in the ammonia concentration detection accuracy can be suppressed.

Also, the ECU 200 receives from the control section 3 the concentrations of NO, $NO_2$, and ammonia contained in the exhaust gas having passed through the SCR 522, and performs various types of controls for the engine, deterioration judgment for the DOC 512, regeneration control for the DPF 514, urea water addition control, etc. As a result, on the basis of the results of the detection by the control section 3 (the concentrations of NO, $NO_2$, and ammonia), the ECU 200 can properly judge the state of the exhaust gas and can properly execute the various types of controls for the engine, deterioration judgment for the DOC 512, regeneration control for the DPF 514, urea water addition control, etc.

4-5. Correspondence Between Embodiment and Claims

A description will be given of the correspondence between terms used in claims and terms used in the present embodiment.

The separate-type sensor 540 corresponds to an example of the sensor; the $NO_x$ sensor 541 corresponds to an example of the $NO_x$ sensor section; the ammonia sensor 542 corresponds to an example of the ammonia sensor section; and the sensor control apparatus 301 corresponds to an example of the sensor control apparatus. The exhaust pipe 502 (exhaust path 502) corresponds to an example of the exhaust path; and the catalyst 512, the particulate filter 514, the selective-reduction-type catalyst 522, and the subsequent stage oxidation catalyst 524 correspond to an example of the partition portions.

5. Other Embodiments

Although embodiments of the present invention have been described, the present invention is not limited to the above-described embodiments, and the present invention can be implemented in various forms without departing from the technical scope of the present invention.

For example, in the above-described first embodiment and modified embodiment 2, the judgment as to whether or not a predetermined stop period has elapsed is made by executing S220, S230, and S240 in the gas concentration computation processing. However, S220, S230, and S240 may be omitted as steps in the gas concentration computation processing.

Namely, instead of stopping the computation of the corrected ammonia concentration and the update of the "$NH_3$ concentration (this time)" until the stop period elapses after a negative judgment has been made in S200, the computation of the corrected ammonia concentration and the update of the "$NH_3$ concentration (this time)" may continue. As a result, the computation of the corrected ammonia concentration is repeatedly performed and the update of the "$NH_3$ concentration (this time)" is continued depending on the result of the judgment in S200, whereby a decrease in the ammonia concentration detection accuracy can be suppressed.

Also, in the above-described first embodiment and modified embodiment 2, in the gas concentration computation processing, S160 is executed, and when a negative judgment is made in S160, S170 is executed. However, the above-described first embodiment and modified embodiment 2 may be modified to execute S170 after executing S150 as a step in the gas concentration computation processing, and then execute S160.

Namely, the above-described first embodiment and modified embodiment 2 may be modified such that, after having computed the oxygen concentration in S150, the CPU 61 proceeds to S170 so as to first compute the "$NH_3$ concentration (this time)," the "$NO_2$ concentration (this time)," and the "NO concentration (this time)," and then proceeds to S160 so as to judge whether or not a value is stored in the "$O_2$ concentration (last time)" which is one of the internal variables used for the computation by the CPU 61. Notably, in this gas concentration computation processing, when the CPU 61 makes a negative judgment in S160 or makes an affirmative judgment in S200, the CPU 61 proceeds to S180.

Also, the above-described first embodiment and modified embodiment 2 are configured such that the correction permission condition in S200 of the gas concentration computation processing is determined on the basis of the oxygen concentration and the oxygen concentration change rate. However, the configurations of the above-described first embodiment and modified embodiment 2 are not limited to such a configuration. For example, the correction permission condition may be determined on the basis of the oxygen concentration change rate only. Specifically, when the CUP may judge in S200 that the correction permission condition is satisfied (affirmative judgment) when the oxygen concentration change rate is less than the predetermined reference judgment value and that the correction permission condition is not satisfied (negative judgment) when the oxygen concentration change rate is equal to or greater than the reference judgment value.

Namely, since the oxygen concentration change rate increases with the degree of steepness of a change in the oxygen concentration, when the oxygen concentration change rate is equal to or greater than the reference judgment value, it is possible to determine that the oxygen concentration has changed sharply and judge that the correction permission condition is not satisfied. Therefore, even when the correction permission condition is determined on the basis of the oxygen concentration change rate only, it is possible to judge whether or not the detection error of the ammonia concentration falls within the allowable range when the corrected ammonia concentration is computed.

Also, the engine to which the multi-gas sensor control apparatus of the present invention is applied is not limited to the above-described diesel engine, and the multi-gas sensor control apparatus may be applied to a gasoline engine. No particular limitation is imposed on the type of the engine.

Next, in the above-described modified embodiment 3, the separate-type sensor 540 including the $NO_x$ sensor 541 and the ammonia sensor 542 provided separately is configured such that the $NO_x$ sensor 541 is disposed on the upstream side of the ammonia sensor 542 in the flow direction of the exhaust gas. However, the configuration of the separate-type sensor 540 is not limited to such a configuration.

Figure 12:
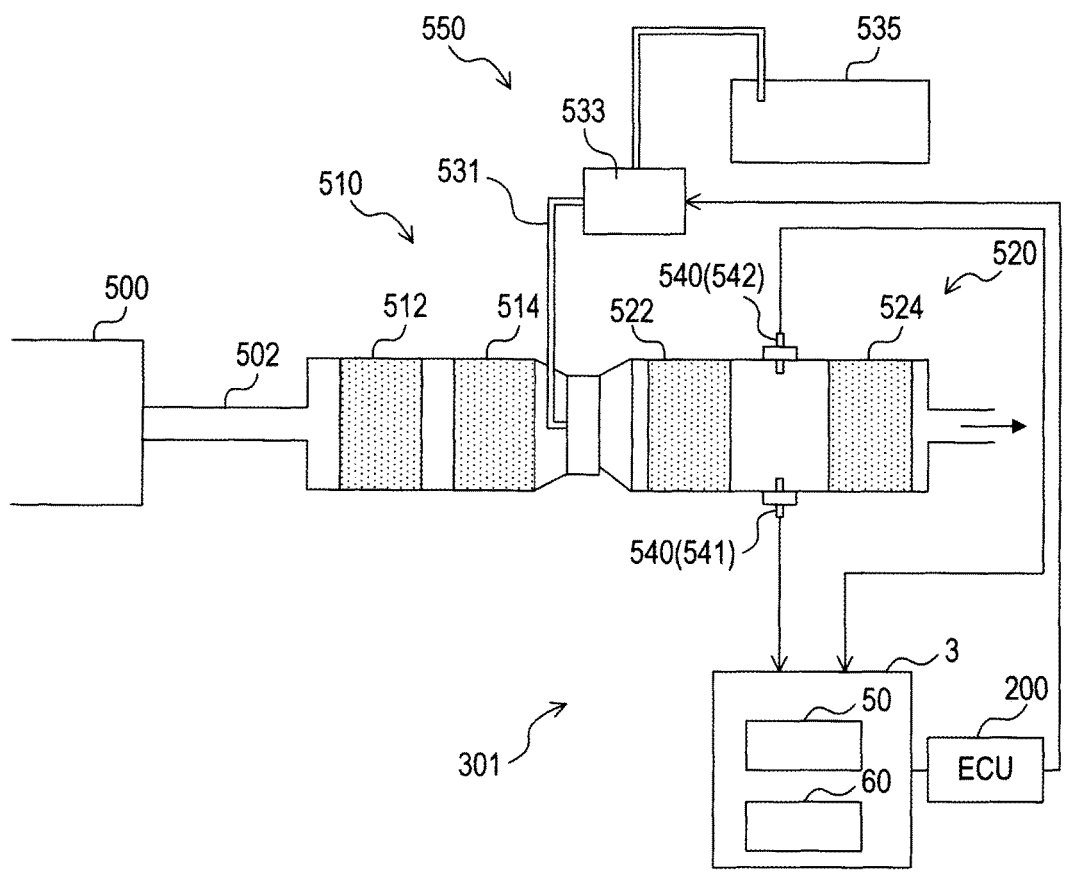
FIG. 12 is a block diagram describing the configuration of a sensor control apparatus of a modified embodiment 4.

For example, as in a modified embodiment 4 shown in FIG. 12, the separate-type sensor 540 may be configured such that the $NO_x$ sensor 541 is disposed at the same position as the ammonia sensor 542 in the flow direction of the exhaust gas. Notably, in this case as well, the $NO_x$ sensor 541 and the ammonia sensor 542 are disposed in the same space of the exhaust path S502.

Since the relative positional relationship between the $NO_x$ sensor 541 and the ammonia sensor 542 is determined in this manner, the oxygen concentration detection position is located at the same positon as the ammonia concentration detection position in the flow direction of the exhaust gas. In this case, in computation of the corrected ammonia concentration, the oxygen concentration detected at the same position as the ammonia concentration detection position can be used. As a result, the detection timing of the oxygen concentration does not fall behind the detection timing of the ammonia concentration, and the corrected ammonia concentration can be computed accurately.

Therefore, according to this sensor control apparatus, the corrected ammonia concentration is computed accurately, whereby a decrease in the ammonia concentration detection accuracy can be suppressed.

DESCRIPTION OF REFERENCE NUMERALS

1: multi-gas sensor control apparatus, 2: multi-gas sensor, 3: control section (computation section), 10: sensor element section, 11: $NO_x$ sensor section, 12: first pumping cell, 12a: first solid electrolyte member, 12b: inner first pumping electrode, 12c: outer first pumping electrode, 16: oxygen concentration detection cell, 16a: third solid electrolyte member, 16b: detection electrode, 16c: reference electrode, 18: second pumping cell, 18a: second solid electrolyte member, 18b: inner second pumping electrode, 18c: second pumping counterpart electrode, 19: heater, 21: ammonia sensor section, 21a: electrode, 21a1: detection electrode, 21a2: reference electrode, 60: microcomputer, 61: CPU, 62: RAM, 63: ROM, 64: signal input/output section, 301: sensor control apparatus, 540: separate-type sensor, 541: $NO_x$ sensor, 542: ammonia sensor.

What is claimed is:

1. A sensor control method for controlling a sensor comprising:
    providing an $NO_x$ sensor section having a first pumping cell which pumps out oxygen contained in a gas under measurement introduced into a measurement chamber and pumps oxygen into the measurement chamber, and a second pumping cell through which a second pumping current flows in accordance with a concentration of $NO_x$ contained in the gas under measurement whose oxygen concentration has been adjusted by the first pumping cell;
    providing an ammonia sensor section and which outputs an ammonia concentration signal representing a concentration of ammonia contained in the gas under measurement;
    an oxygen concentration computation step of computing an oxygen concentration contained in the gas under measurement on the basis of a first pumping current flowing through the first pumping cell;
    a corrected concentration computation step of computing a primary corrected ammonia concentration on the basis of the oxygen concentration and the ammonia concentration signal output from the ammonia sensor section;
    an oxygen concentration change rate computation step of computing an oxygen concentration change rate which is the rate of change of the oxygen concentration with elapse of time; and
    an ammonia concentration setting step in which it is determined if a predetermined correction permission condition is satisfied, with the predetermined correction permission condition being satisfied when the oxygen concentration change rate is less than a predetermined reference judgment value and the predetermined correction permission condition being not satisfied when the oxygen concentration change rate is equal to or greater than the reference judgment value;
    wherein, when the predetermined correction permission condition is satisfied, the primary corrected ammonia concentration is set to a detection result of the ammonia concentration, and when the correction permission condition is not satisfied, among a plurality of corrected ammonia concentrations computed in the past, a previous corrected ammonia concentration computed when the correction permission condition was satisfied is set to the detection result of the ammonia concentration.

2. A sensor control method according to claim 1, wherein in the ammonia concentration setting step, when the correction permission condition is not satisfied, among the plurality of corrected ammonia concentrations computed in the past, a latest corrected ammonia concentration computed when the correction permission condition was satisfied is set to the detection result of the ammonia concentration.

3. A sensor control method according to claim 1, wherein in the ammonia concentration setting step, when the correction permission condition is not satisfied, an immediately prior detection result of the ammonia concentration is set to the detection result of the ammonia concentration.

4. A sensor control method according to claim 1, wherein in the ammonia concentration setting step, the correction permission condition is satisfied when the oxygen concentration change rate is less than the reference judgment value and the oxygen concentration exceeds a predetermined reference concentration, and the correction permission condition is not satisfied when the oxygen concentration change rate is equal to or greater than the reference judgment value or the oxygen concentration is equal to or less than the reference concentration.

5. A sensor control method according to claim 1, wherein in the ammonia concentration setting step, the correction permission condition is not satisfied unless a predetermined stop period elapses after a previous correction permission condition has been judged to be not satisfied.

6. A sensor control method according to claim 1, wherein in the oxygen concentration change rate computation step, the oxygen concentration change rate is computed by dividing an immediately prior oxygen concentration by the oxygen concentration.

7. A sensor control method according to claim 1, wherein the $NO_x$ sensor section and the ammonia sensor section are integrated together to form a multi-gas sensor.

8. A sensor control method according to claim 1, wherein the $NO_x$ sensor section and the ammonia sensor section are provided separately and disposed in an exhaust path of an internal combustion engine, the exhaust path including a plurality of spaces separated from one another by partition portions through which exhaust gas can pass; and
    the $NO_x$ sensor section and the ammonia sensor section are disposed in a same space among the plurality of spaces.

9. A sensor control method according to claim 8, wherein the $NO_x$ sensor section is disposed at the same position as the ammonia sensor section or on an upstream side of the ammonia sensor section in a flow direction of the exhaust gas.

10. A sensor control apparatus for controlling a sensor which includes an $NO_x$ sensor section having a first pumping cell which pumps out oxygen contained in a gas under measurement introduced into a measurement chamber and pumps oxygen into the measurement chamber, and a second pumping cell through which a second pumping current flows in accordance with a concentration of $NO_x$ contained in the gas under measurement whose oxygen concentration has been adjusted by the first pumping cell, and an ammonia sensor section and which outputs an ammonia concentration signal representing a concentration of ammonia contained in the gas under measurement, the sensor control apparatus comprising a microcomputer programmed to:

compute an oxygen concentration contained in the gas under measurement on the basis of a first pumping current flowing through the first pumping cell;

compute a primary corrected ammonia concentration on the basis of the oxygen concentration and the ammonia concentration signal output from the ammonia sensor section;

compute an oxygen concentration change rate which is the rate of change of the oxygen concentration with elapse of time; and determine if a predetermined correction permission condition is satisfied, with the predetermined correction permission condition being satisfied when the oxygen concentration change rate is less than a predetermined reference judgement value and the predetermined correction permission condition being not satisfied when the oxygen concentration change rate is equal to or greater than the reference judgment value;

wherein, when the predetermined correction permission condition is satisfied, the microcomputer is programmed to set the primary corrected ammonia concentration to a detection result of the ammonia concentration, and when the predetermined correction permission condition is not satisfied, the microcomputer is programmed to set the detection result of the ammonia concentration, among a plurality of corrected ammonia concentrations computed in the past, a previously corrected ammonia concentration computed when the correction permission condition was satisfied.

11. A sensor control apparatus according to claim 10, wherein when the correction permission condition is not satisfied, the microcomputer is programmed to set to the detection result of the ammonia concentration, among the corrected ammonia concentrations computed in the past, a latest corrected ammonia concentration computed when the oxygen concentration change rate satisfied the correction permission condition.

12. A sensor control apparatus according to claim 10, wherein when the correction permission condition is not satisfied, the microcomputer is programmed to set an immediately prior detection result of the ammonia concentration to the detection result of the ammonia concentration.

13. A sensor control apparatus according to claim 10, wherein the correction permission condition is satisfied when the oxygen concentration change rate is less than the reference judgment value and the oxygen concentration exceeds a predetermined reference concentration, and the correction permission condition is not satisfied when the oxygen concentration change rate is equal to or greater than the reference judgment value or the oxygen concentration is equal to or less than the predetermined reference concentration is satisfied.

14. A sensor control apparatus according to claim 10, including the $NO_x$ sensor section and the ammonia sensor section integrated to from a multi-gas sensor.

15. A sensor control apparatus according to claim 10, including the $NO_x$ sensor section and the ammonia sensor section provided separately and disposed in an exhaust path of an internal combustion, the exhaust path including a plurality of spaces separated from one another by partition portions through which exhaust gas can pass; and the $NO_x$ sensor section and the ammonia sensor section disposed in a same space among the plurality of spaces.

16. A sensor control apparatus according to claim 15, wherein the $NO_x$ sensor section is disposed at the same position as the ammonia sensor section or on an upstream side of the ammonia sensor section in a flow direction of the exhaust gas.

* * * * *